United States Patent
Davis et al.

(10) Patent No.: US 10,196,648 B2
(45) Date of Patent: Feb. 5, 2019

(54) PLANT REGULATORY ELEMENTS AND USES THEREOF

(71) Applicant: Monsanto Technology LLC, St. Louis, MO (US)

(72) Inventors: Ian W. Davis, Durham, NC (US); Aabid Shariff, Durham, NC (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/874,158

(22) Filed: Jan. 18, 2018

(65) Prior Publication Data

US 2018/0216129 A1  Aug. 2, 2018

Related U.S. Application Data

(60) Provisional application No. 62/448,019, filed on Jan. 19, 2017.

(51) Int. Cl.
*C12N 15/82* (2006.01)
*C12N 5/04* (2006.01)
*C12N 9/24* (2006.01)

(52) U.S. Cl.
CPC .......... *C12N 15/8274* (2013.01); *C12N 5/04* (2013.01); *C12N 9/2402* (2013.01); *C12N 15/8261* (2013.01); *C12N 15/8279* (2013.01); *C12Y 302/01031* (2013.01)

(58) Field of Classification Search
None
See application file for complete search history.

(56) References Cited

U.S. PATENT DOCUMENTS

| | | | |
|---|---|---|---|
| 2008/0168583 A1* | 7/2008 | Fincher | C07K 14/415 800/278 |
| 2013/0096032 A1 | 4/2013 | Bush et al. | |
| 2014/0283201 A1 | 9/2014 | Flasinski et al. | |
| 2016/0298127 A1 | 10/2016 | Ahrens et al. | |

FOREIGN PATENT DOCUMENTS

| | | |
|---|---|---|
| WO | WO 2001/098480 | 12/2001 |
| WO | WO 2012/006426 | 1/2012 |
| WO | WO 2014/004638 | 1/2014 |

OTHER PUBLICATIONS

International Search Report and Written Opinion regarding International Application No. PCT/US2018/014155, dated May 21, 2018.

* cited by examiner

*Primary Examiner* — Vinod Kumar
(74) *Attorney, Agent, or Firm* — Dentons US LLP; Carine M. Doyle, Esq.

(57) ABSTRACT

The invention provides recombinant DNA molecules and constructs, as well as their nucleotide sequences, useful for modulating gene expression in plants. The invention also provides transgenic plants, plant cells, plant parts, and seeds comprising the recombinant DNA molecules operably linked to heterologous transcribable DNA molecules, as are methods of their use.

15 Claims, No Drawings
Specification includes a Sequence Listing.

PLANT REGULATORY ELEMENTS AND USES THEREOF

REFERENCE TO RELATED APPLICATION

This application claims the benefit of U.S. Provisional Application No. 62/448,019, filed Jan. 19, 2017, which is herein incorporated by reference in its entirety.

INCORPORATION OF SEQUENCE LISTING

The computer readable form of the sequence listing that is contained in the file named "MONS436US-sequence_listing.txt" is 59,917 bytes (as measured in Microsoft Windows®) and was created on Jan. 12, 2018, is filed by electronic submission concurrently with this application and is herein incorporated by reference in its entirety.

FIELD OF THE INVENTION

The invention relates to the field of plant molecular biology and plant genetic engineering. More specifically, the invention relates to DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the field of plant molecular biology and plant genetic engineering.

SUMMARY OF THE INVENTION

The invention provides novel synthetic gene regulatory elements for use in plants. The invention also provides recombinant DNA molecules and constructs comprising the regulatory elements. The present invention also provides transgenic plant cells, plants, and seeds comprising the synthetic regulatory elements. In one embodiment, the synthetic regulatory elements are operably linked to a heterologous transcribable DNA molecule. The present invention also provides methods of using the synthetic regulatory elements and methods of making and using the recombinant DNA molecules comprising the synthetic regulatory elements and transgenic plant cells, plants, and seeds comprising the synthetic regulatory elements operably linked to a transcribable DNA molecule.

Thus, in one aspect, the invention provides a recombinant DNA molecule comprising a DNA sequence selected from the group consisting of: (a) a sequence with at least 85 percent sequence identity to any of SEQ ID NOs:1-29 and 43-45; (b) a sequence comprising any of SEQ ID NOs:1-29 and 43-45; and (c) a fragment of any of SEQ ID NOs:1-29 and 43-45, wherein the fragment has gene-regulatory activity; wherein the sequence is operably linked to a heterologous transcribable DNA molecule. By "heterologous transcribable DNA molecule," it is meant that the transcribable DNA molecule is heterologous with respect to the polynucleotide sequence to which it is operably linked. In specific embodiments, the recombinant DNA molecule comprises a DNA sequence having at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:1-29 and 43-45. In particular embodiments, the DNA sequence comprises a regulatory element. In some embodiments the regulatory element comprises a promoter. In still other embodiments, the heterologous transcribable DNA molecule comprises a gene of agronomic interest, such as a gene capable of providing herbicide resistance in plants, or a gene capable of providing plant pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: (a) a sequence with at least about 85 percent sequence identity to any of SEQ ID NOs:1-29 and 43-45; (b) a sequence comprising any of SEQ ID NOs:1-29 and 43-45; and (c) a fragment of any of SEQ ID NOs:1-29 and 43-45, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a sequence with at least 85 percent sequence identity to any of SEQ ID NOs:1-29 and 43-45; b) a sequence comprising any of SEQ ID NOs:1-29 and 43-45; and c) a fragment of any of SEQ ID NOs:1-29 and 43-45, wherein the fragment has gene-regulatory activity; wherein the sequence is operably linked to a heterologous transcribable DNA molecule. In specific embodiments, the transgenic plant is a progeny plant of any generation that comprises the recombinant DNA molecule. A transgenic seed comprising the recombinant DNA molecule that produces such a transgenic plant when grown is also provided herein.

In another aspect, the invention provides a method of producing a commodity product comprising obtaining a transgenic plant or part thereof containing a recombinant DNA molecule of the invention and producing the commodity product therefrom. In one embodiment, the commodity product is processed seeds, grains, plant parts, oils and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

BRIEF DESCRIPTION OF THE SEQUENCES

SEQ ID NO:1 is a DNA sequence of a synthetic regulatory expression elements group (EXP), EXP-At.GSP442.nno+At.Cyco:3 comprising a synthetic promoter (P-At.GSP442.nno:2), operably linked 5' to a synthetic leader (L-At.GSP442.nno:1), operably linked 5' to an intron (I-At.Cyco:2).

SEQ ID NO:2 is a synthetic promoter sequence, P-At.GSP442.nno:2.

SEQ ID NO:3 is a synthetic leader sequence, L-At.GSP442.nno:1.

SEQ ID NO:4 is a DNA sequence of a synthetic EXP, EXP-At.GSP571 comprising a synthetic promoter (P-At.GSP571.nno:5), operably linked 5' to a synthetic leader (L-At.GSP571.nno:1).

SEQ ID NO:5 is a synthetic promoter sequence, P-At.GSP571.nno:5.

SEQ ID NO:6 is a synthetic leader sequence, L-At.GSP571.nno:1.

SEQ ID NO:7 is a DNA sequence of a synthetic regulatory expression elements group (EXP), EXP-At.GSP571.nno+At.Cyco:2 comprising a synthetic promoter (P-At.GSP571.nno:5), operably linked 5' to a synthetic leader (L-At.GSP571.nno:1), operably linked 5' to an intron (I-At.Cyco:2).

SEQ ID NO:8 is a DNA sequence of a synthetic regulatory expression elements group (EXP), EXP-At.GSP571.nno+At.GSI21.nno:10 comprising a synthetic promoter (P-At.GSP571.nno:5), operably linked 5' to a synthetic leader (L-At.GSP571.nno:1), operably linked 5' to a synthetic intron (I-At.GSI21.nno:2).

SEQ ID NO:9 is a synthetic intron sequence, I-At.GSI21.nno:2.

SEQ ID NO:10 is a DNA sequence of a synthetic EXP, EXP-At.GSP571.nno+At.GSI102.nno:1 comprising a synthetic promoter (P-At.GSP571.nno:5), operably linked 5' to a synthetic leader (L-At.GSP571.nno:1), operably linked 5' to a synthetic intron (I-At.GSI102.nno:1).

SEQ ID NO:11 is a synthetic intron sequence, I-At.GSI102.nno:1.

SEQ ID NO:12 is a DNA sequence of a synthetic EXP, EXP-At.GSP564 comprising a synthetic promoter (P-At.GSP564.nno:3), operably linked 5' to a synthetic leader (L-At.GSP564.nno: 1).

SEQ ID NO:13 is a synthetic promoter sequence, P-At.GSP564.nno:3.

SEQ ID NO:14 is a synthetic leader sequence, L-At.GSP564.nno:1.

SEQ ID NO:15 is a DNA sequence of a synthetic EXP, EXP-At.GSP564.nno+At.Cyco:2 comprising a synthetic promoter (P-At.GSP564.nno:3), operably linked 5' to a synthetic leader (L-At.GSP564.nno:1), operably linked 5' to an intron (I-At.Cyco:2).

SEQ ID NO:16 is a DNA sequence of a synthetic EXP, EXP-At.GSP564.nno+At.GSI17.nno:2 comprising a synthetic promoter (P-At.GSP564.nno:3), operably linked 5' to a synthetic leader (L-At.GSP564.nno:1), operably linked 5' to a synthetic intron (I-At.GSI17.nno:1).

SEQ ID NO:17 is a synthetic intron sequence, I-At.GSI17.nno:1.

SEQ ID NO:18 is a DNA sequence of a synthetic EXP, EXP-At.GSP564.nno+At.GSI102.nno:1 comprising a synthetic promoter (P-At.GSP564.nno:3), operably linked 5' to a synthetic leader (L-At.GSP564.nno:1), operably linked 5' to a synthetic intron (I-At.GSI102.nno:1).

SEQ ID NO:19 is a DNA sequence of a synthetic EXP, EXP-At.GSP579 comprising a synthetic promoter (P-At.GSP579.nno:2), operably linked 5' to a synthetic leader (L-At.GSP579.nno: 1).

SEQ ID NO:20 is a synthetic promoter sequence, P-At.GSP579.nno:2.

SEQ ID NO:21 is a synthetic leader sequence, L-At.GSP579.nno:1.

SEQ ID NO:22 is a DNA sequence of a synthetic EXP, EXP-At.GSP579.nno+At.GSI102.nno:3 comprising a synthetic promoter (P-At.GSP579.nno:2), operably linked 5' to a synthetic leader (L-At.GSP579.nno:1), operably linked 5' to synthetic intron (I-At.GSI102.nno:1).

SEQ ID NO:23 is a DNA sequence of a synthetic EXP, EXP-At.GSP571.nno+At.GSP442.nno+At.Cyco:1 comprising a synthetic chimeric promoter (P-At.GSP571/442, which is comprised of a synthetic enhancer (E-At.GSP571.nno:1) operably linked 5' to a synthetic promoter (P-At.GSP442.nno:2)), operably linked 5' to a synthetic leader (L-At.GSP442.nno:1), operably linked 5' to a leader (L-At.Cyco-1:1:2), operably linked 5' to an intron (I-At.Cyco:2).

SEQ ID NO:24 is a synthetic enhancer sequence, E-At.GSP571.nno:1.

SEQ ID NO:25 is a DNA sequence of a synthetic chimeric promoter, P-At.GSP571/442 comprised of a synthetic enhancer (E-At.GSP571.nno:1) operably linked 5' to a synthetic promoter (P-At.GSP442.nno:2).

SEQ ID NO:26 is a DNA sequence of a synthetic EXP, EXP-At.GSP576.nno+At.GSI17.nno:3 comprising a synthetic promoter (P-At.GSP576.nno:4), operably linked 5' to a synthetic leader (L-At.GSP576.nno:2), operably linked 5' to synthetic intron (I-At.GSI17.nno:1).

SEQ ID NO:27 is a synthetic promoter sequence, P-At.GSP576.nno:4.

SEQ ID NO:28 is a synthetic leader sequence, L-At.GSP576.nno:2.

SEQ ID NO:29 is a synthetic 3' UTR, T-Zm.GST59.nno:1.

SEQ ID NO:30 is a DNA sequence of a synthetic EXP, EXP-At.GSP221+At.Cyco:3 comprising a synthetic promoter (P-At.GSP221:3), operably linked 5' to a synthetic leader (L-At.GSP221:1), operably linked 5' to an intron (I-At.Cyco:2).

SEQ ID NO:31 is a synthetic promoter sequence, P-At.GSP221:3.

SEQ ID NO:32 is a synthetic leader sequence, L-At.GSP221:1.

SEQ ID NO:33 is an intron sequence, I-At.Cyco:2 derived from a Cytochrome c oxidase subunit VIa gene from *Arabidopsis*.

SEQ ID NO:34 is a 3' UTR sequence, T-Mt.Sali3-2-1:2:1 derived from the Sali3 gene of *Medicago truncatula*.

SEQ ID NO:35 is a 3' UTR sequence, T-Mt.Oxr-1:2:1 derived from a putative oxidoreductase (OXR) protein gene from *Medicago truncatula*.

SEQ ID NO:36 is a 3' UTR sequence, T-Gb.FbL2:1 derived from the *Gossypium barbadense* FbLate-2 gene.

SEQ ID NO:37 is a 3' UTR sequence, T-Mt.RD22-1:2:1 derived from a dehydration-responsive protein RD22 gene from *Medicago truncatula*.

SEQ ID NO:38 is a DNA sequence of an EXP derived from a Cytochrome c oxidase subunit VIa gene from *Arabidopsis*, EXP-At.Cyco:1:1 comprising a promoter (P-At.Cyco-1:1:2), operably linked 5' to a leader (L-At.Cyco-1:1:2), operably linked 5' to intron (I-At.Cyco-1:1:1).

SEQ ID NO:39 is a promoter sequence, P-At.Cyco-1:1:2 derived from a Cytochrome c oxidase subunit VIa gene from *Arabidopsis*.

SEQ ID NO:40 is a leader sequence, L-At.Cyco-1:1:2 derived from a Cytochrome c oxidase subunit VIa gene from *Arabidopsis*.

SEQ ID NO:41 is an intron sequence, I-At.Cyco-1:1:1 derived from a Cytochrome c oxidase subunit VIa gene from *Arabidopsis*.

SEQ ID NO:42 is a coding sequence for β-glucuronidase (GUS) with a processable intron derived from the potato light-inducible tissue-specific ST-LS1 gene (Genbank Accession: X04753).

SEQ ID NO:43 is a DNA sequence of an EXP, EXP-At.GSP442+L-I-At.Cyco comprising the synthetic promoter, P-At.GSP442.nno:2, operably linked 5' to the synthetic leader, L-At.GSP442.nno:1, operably linked 5' to the leader, L-At.Cyco-1:1:2, which is operably linked 5' to the intron, I-At.Cyco:2.

SEQ ID NO:44 is a DNA sequence of the synthetic 3' UTR, T-Zm.GST7.nno:2.

SEQ ID NO:45 is a DNA sequence of an EXP, EXP-At.GSP576.nno+At.Cyco:1 comprising the synthetic promoter, P-At.GSP564.nno:3, operably linked 5' to the synthetic leader, L-At.GSP564.nno:1, which is operably linked 5' to the intron, I-At.Cyco:2.

SEQ ID NO:46 is a DNA sequence of the EXP, EXP-CaMV.35S comprising the 35S promoter and leader derived from the *Cauliflower mosaic virus*.

SEQ ID NO:47 is a DNA sequence of the intron, I-Zm.DnaK:1, derived from the heat shock protein 70 (Hsp70) gene (DnaK) from *Zea mays*.

SEQ ID NO:48 is a DNA sequence of the 3' UTR, T-Os.LTP:1, derived from the Lipid Transfer Protein-like gene (LTP) from *Oryza sativa*.

SEQ ID NO:49 is a coding sequence for the NanoLuc® luciferase fluorescent protein (Promega, Madison, Wis. 53711), Nluc which was engineered by directed evolution from a deep-sea shrimp (*Oplophorus gacilirostris*) luciferase.

SEQ ID NO:50 is a DNA sequence of the EXP, EXP-At.Bglu21+At.Cyco:2 comprising the promoter and leader of a beta-glucuronidase 21 gene from *Arabidopsis thaliana*, operably linked 5' to the intron, I-At.Cyco-1:1:1.

SEQ ID NO:51 is a DNA sequence of the EXP, EXP-CaMV.35S-enh+Ph.DnaK:1:3 comprising an enhanced *Cauliflower mosaic virus* 35S promoter, operably linked 5' to the leader of the heat shock protein 70 (HSP70) gene from *Petunia x hybrid*.

SEQ ID NO:52 is a DNA sequence of the EXP, EXP-Gm.Sphas1:1:1 comprising the promoter and leader of the 7S alpha prime gene of soybean.

SEQ ID NO:53 is a DNA sequence of the EXP, EXP-CaMV.35S-enh+Zm.DnaK:1:1 comprising an enhanced *Cauliflower mosaic virus* 35S promoter, operably linked 5' to the intron, I-Zm.DnaK:1.

SEQ ID NO:54 is a DNA sequence encoding a luciferase protein (LUCIFERASE:1:3) derived from *Photinus pyralis* (Firefly).

SEQ ID NO:55 is a DNA sequence of the 3' UTR, T-AGRtu.nos-1:1:13 derived from the *Agrobacterium tumefaciens* nopaline synthase gene.

SEQ ID NO:56 is a DNA sequence of the EXP, EXP-CaMV.35S-enh-Lhcb1 comprising an enhanced *Cauliflower mosaic virus* 35S promoter, operably linked 5' to the leader of a chlorophyll a/b-binding gene of the light-harvesting complex of *Triticum aestivum* (Wheat).

SEQ ID NO:57 is a DNA sequence encoding a luciferase protein (CR-Ren.h*Renilla* Lucife-0:0:1) derived from *Renilla reniformis* (Sea Pansy).

DETAILED DESCRIPTION OF THE INVENTION

The invention provides synthetic regulatory elements having gene-regulatory activity in plants. The nucleotide sequences of these synthetic regulatory elements are provided as SEQ ID NOs:1-29 and SEQ ID NOs:43-45. These synthetic regulatory elements are capable of affecting the expression of an operably linked transcribable DNA molecule in plant tissues, and therefore regulating gene expression of an operably linked transgene in transgenic plants. The invention also provides methods of modifying, producing, and using recombinant DNA molecules which contain the provided synthetic regulatory elements. The invention also provides compositions that include transgenic plant cells, plants, plant parts, and seeds containing the recombinant DNA molecules of the invention, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, a DNA molecule that comprises a synthetic DNA sequence or a DNA molecule that has been incorporated into a host cell's DNA by genetic transformation or gene editing.

As used herein, a "synthetic nucleotide sequence" or "artificial nucleotide sequence" is a nucleotide sequence that is not known to occur in nature, that is not naturally occurring, or that does not occur without human intervention. The gene-regulatory elements of the present invention comprise synthetic nucleotide sequences. Preferably, synthetic nucleotide sequences share little or no extended homology to natural sequences. Extended homology in this context generally refers to 100% sequence identity extending beyond about 25 nucleotides of contiguous sequence.

Reference in this application to an "isolated DNA molecule," or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as SEQ ID NOs:1-29 and SEQ ID NOs:43-45.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as any of SEQ ID NOs:1-29 and SEQ ID NOs:43-45, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence. In still further specific embodiments, a sequence having a percent identity to any of SEQ ID NOs:1-29 and SEQ ID NOs:43-45 may be defined as exhibiting promoter activity possessed by the starting sequence from which it is derived. A sequence having a percent identity to any of SEQ ID NOs:1-29 and SEQ ID NOs:43-45 may further comprise a "minimal promoter" which provides a basal level of transcription and is comprised of a TATA box or equivalent sequence for recognition and binding of the RNA polymerase II complex for initiation of transcription.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering.

As used herein, a "regulatory expression element group" or "EXP" sequence may refer to a group of operably linked regulatory elements, such as enhancers, promoters, leaders, and introns. For example, a regulatory expression element group may be comprised, for instance, of a promoter operably linked 5' to a leader sequence. EXP's useful in practicing the present invention include SEQ ID NOs:1, 4, 7, 8, 10, 12, 15, 16, 18, 19, 22, 23, 26, 30, 43 and 45.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a micro-RNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene. Alternately, promoters may be synthetically produced or manipulated DNA molecules. Promoters may also be chimeric. Chimeric promoters are produced through the fusion of two or more heterologous DNA molecules. Promoters useful in practicing the present invention include promoter elements comprised within any of SEQ ID NOs:2, 5, 13, 20, 25, 27, 31 and 39 or fragments or variants thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and promoter fragments, such as in constructing chimeric promoters, or in combination with other expression elements and expression element fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. In certain embodiments, the invention provides fragments of a promoter provided herein, having the activity of the full length sequence. Methods for producing such fragments from a starting promoter molecule are well known in the art.

Compositions derived from any of the promoter elements comprised within any of SEQ ID NOs:2, 5, 13, 20, 25, 27, 31 and 39, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoter elements comprised within any of SEQ ID NOs:2, 5, 13, 20, 25, 27, 31 and 39 comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. Any of the promoter elements comprised within any of SEQ ID NOs:2, 5, 13, 20, 25, 27, 31 and 39 and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Leaders useful in practicing the present invention include SEQ ID NOs:3, 6, 14, 21, 28, 32 and 40; or any of the leader elements comprised within any of SEQ ID NOs:1, 4, 7, 8, 10, 12, 15, 16, 18, 19, 22, 23, 26, 30, 43 and 45 or fragments or variants thereof. In specific embodiments, such DNA sequences may be defined as being capable of acting as a leader in a host cell, including, for example, a transgenic plant cell. In one embodiment, such sequences are decoded as comprising leader activity.

The leader sequences (also referred to as 5' UTRs) presented as SEQ ID NOs:3, 6, 14, 21, 28, 32 and 40 or any of the leader elements comprised within any of SEQ ID NOs:1, 4, 7, 8, 10, 12, 15, 16, 18, 19, 22, 23, 26, 30 and 43 may be comprised of regulatory elements, or may adopt secondary structures that can have an effect on transcription or translation of an operably linked transcribable DNA molecule. The leader sequences presented as SEQ ID NOs:3, 6, 14, 21, 28, 32 and 40 or any of the leader elements comprised within any of SEQ ID NOs:1, 4, 7, 8, 10, 12, 15, 16, 18, 19, 22, 23, 26, 30, 43 and 45 can be used in accordance with the invention to make chimeric regulatory elements that affect transcription or translation of a an operably linked transcribable DNA molecule.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns known in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements. Exemplary introns useful in practicing the present invention are presented as SEQ ID NOs:9, 11, 17, 33 and 41.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. First, the 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. Second, the 3' UTR should not cause a reduction in the transcriptional activity imparted by the promoter, leader, enhancers, and introns that are used to drive expression of the DNA molecule. Finally, in plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette. A 3' UTR useful in practicing the present invention is presented as SEQ ID NOs:29, 34, 35, 36, 37, and 44.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression. An example of an enhancer element derived from the synthetic promoter, P-At.GSP571.nno:5 (SEQ ID NO:5) is provided as SEQ ID NO:24 (E-At.GSP571.nno:1).

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting; methylation interference; electrophoresis mobility-shift assays; in vivo genomic footprinting by ligation-mediated polymerase chain reaction (PCR); and other conventional assays or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention. An exemplary enhancer useful in practicing this invention is presented as SEQ ID NO:24.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments for example, the fusion of a promoter to an enhancer element. Thus, the design, construction, and use of chimeric promoters according to the methods disclosed herein for modulating the expression of operably linked transcribable DNA molecules are encompassed by the present invention. An exemplary chimeric promoter is presented herein as SEQ ID NO:25 (P-At.GSP571/442).

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, the DNA sequences provided as SEQ ID NOs:1-29 and SEQ ID NOs:43-45 may provide regulatory element reference sequences, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule or an altered version of the sequence of the first DNA molecule, such as one with different restriction enzyme sites and/or internal deletions, substitutions, or insertions. A "variant" can also encompass a regulatory element having a nucleotide sequence comprising a substitution, deletion, or insertion of one or more nucleotides of a reference sequence, wherein the derivative regulatory element has more or less or equivalent transcriptional or translational activity than the corresponding parent regulatory molecule. In the present invention, a polynucleotide sequence provided as SEQ ID NOs:1-29 and SEQ ID NOs:43-45 may be used to create variants that are in similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

The efficacy of the modifications, duplications, or deletions described herein on the desired expression aspects of a particular transgene may be tested empirically in stable and transient plant assays, such as those described in the working examples, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404, however other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the *Cauliflower Mosaic Virus* 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a synthetic promoter of the invention, may be operably linked to a heterologous transcribable DNA molecule. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species, or one of the DNA molecules might be synthetic and not found in nature. A regulatory element is heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs:1-29 and SEQ ID NOs:43-45, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include, but are not limited to, those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. U.S. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. U.S. RE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance. An example of a selectable marker transgene is provided as SEQ ID NO:42.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), and gene editing (e.g., CRISPR-Cas systems), among others.

This disclosure further contemplates that the disclosed synthetic expression elements can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the expression element sequence within a plant cell to a different sequence.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique*, (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:1-29 and SEQ ID NOs:43-45. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Design, Synthesis, and Cloning of Synthetic Regulatory Elements

The regulatory elements provided in Table 1 are novel synthetic expression elements designed through algorithmic methods. These computationally-designed synthetic regulatory elements were chemically synthesized and cloned to make synthetic regulatory expression element groups (EXPs). Well over 1,000 synthetic regulatory elements were designed and assayed in soybean protoplasts and stably transformed soybean plants to identify those synthetic regulatory elements that provided desired characteristics, such as protein expression levels and patterns of expression. The synthetic regulatory elements described in Table 1 provide various patterns of expression useful in driving expression of many different coding sequences and interfering RNAs of agronomic interest.

The computationally-designed synthetic regulatory elements do not have extended homology to any known nucleic acid sequences that exist in nature. The synthetic EXPs and the corresponding promoters, leaders, introns and 3' UTRs are presented in Table 1. The synthetic EXPs were cloned using methods known in the art into binary plant transformation vectors, operably linked to a β-glucuronidase (GUS) coding sequence, and the vectors were used to evaluate the levels and patterns of expression provided by the synthetic EXPs in stably transformed soybean, cotton and corn plants.

Analysis of the synthetic regulatory element transcription start site (TSS) and intron/exon splice junctions can be performed using transformed plant tissue. Briefly, the plants are transformed with the plant expression vectors comprising the cloned DNA fragments operably linked to a heterologous transcribable DNA molecule. Next, the 5' RACE System for Rapid Amplification of cDNA Ends, Version 2.0 (Invitrogen, Carlsbad, Calif. 92008) is used to confirm the synthetic regulatory element TSS and intron/exon splice junctions by analyzing the DNA sequence of the produced mRNA transcripts.

TABLE 1

Synthetic transcriptional regulatory expression element groups, promoters, leaders, introns, and 3' UTRs.

| Annotation | SEQ ID NO: | Size (bp) | Description and/or regulatory elements of EXP linked in 5' → 3' direction (SEQ ID NOs): |
|---|---|---|---|
| EXP-At.GSP442.nno + At.Cyco: 3 | 1 | 855 | EXP: P-At.GSP442.nno: 2 (SEQ ID NO: 2), L-At.GSP442.nno: 1 (SEQ ID NO: 3), I-At.Cyco: 2 (SEQ ID NO: 33) |
| P-At.GSP442.nno: 2 | 2 | 480 | Promoter |
| L-At.GSP442.nno: 1 | 3 | 20 | Leader |
| EXP-At.GSP571 | 4 | 500 | EXP: P-At.GSP571.nno: 5 (SEQ ID NO: 5), L-At.GSP571.nno: 1 (SEQ ID NO: 6) |
| P-At.GSP571.nno: 5 | 5 | 451 | Promoter |
| L-At.GSP571.nno: 1 | 6 | 49 | Leader |
| EXP-At.GSP571.nno + At.Cyco: 2 | 7 | 855 | EXP: P-At.GSP571.nno: 5 (SEQ ID NO: 5), L-At.GSP571.nno: 1 (SEQ ID NO: 6), I-At.Cyco: 2 (SEQ ID NO: 33) |
| EXP-At.GSP571.nno + At.GSI21.nno: 10 | 8 | 816 | EXP: P-At.GSP571.nno: 5 (SEQ ID NO: 5), L-At.GSP571.nno: 1 (SEQ ID NO: 6), I-At.GSI21.nno: 2 (SEQ ID NO:9) |
| I-At.GSI21.nno: 2 | 9 | 309 | Intron |
| EXP-At.GSP571.nno + At.GSI102.nno: 1 | 10 | 810 | EXP: P-At.GSP571.nno: 5 (SEQ ID NO: 5), L-At.GSP571.nno: 1 (SEQ ID NO: 6), I-At.GSI102.nno: 1 (SEQ ID NO: 11) |
| I-At.GSI102.nno: 1 | 11 | 310 | Intron |
| EXP-At.GSP564 | 12 | 500 | EXP: P-At.GSP564.nno: 3 (SEQ ID NO: 13), L-At.GSP564.nno: 1 (SEQ ID NO: 14) |

TABLE 1-continued

Synthetic transcriptional regulatory expression element groups, promoters, leaders, introns, and 3' UTRs.

| Annotation | SEQ ID NO: | Size (bp) | Description and/or regulatory elements of EXP linked in 5' → 3' direction (SEQ ID NOs): |
|---|---|---|---|
| P-At.GSP564.nno: 3 | 13 | 461 | Promoter |
| L-At.GSP564.nno: 1 | 14 | 39 | Leader |
| EXP-At.GSP564.nno + At.Cyco: 2 | 15 | 855 | EXP: P-At.GSP564.nno: 3 (SEQ ID NO: 13), L-At.GSP564.nno: 1 (SEQ ID NO: 14), I-At.Cyco: 2 (SEQ ID NO: 33) |
| EXP-At.GSP564.nno + At.GSI17.nno: 2 | 16 | 807 | EXP: P-At.GSP564.nno: 3 (SEQ ID NO: 13), L-At.GSP564.nno: 1 (SEQ ID NO: 14), I-At.GSI17.nno: 1 (SEQ ID NO: 17) |
| I-At.GSI17.nno: 1 | 17 | 300 | Intron |
| EXP-At.GSP564.nno + At.GSI102.nno: 1 | 18 | 810 | EXP: P-At.GSP564.nno: 3 (SEQ ID NO: 13), L-At.GSP564.nno: 1 (SEQ ID NO: 14), I-At.GSI102.nno: 1 (SEQ ID NO: 11) |
| EXP-At.GSP579 | 19 | 500 | EXP: P-At.GSP579.nno: 2 (SEQ ID NO: 20), L-At.GSP579.nno: 1 (SEQ ID NO: 21) |
| P-At.GSP579.nno: 2 | 20 | 449 | Promoter |
| L-At.GSP579.nno: 1 | 21 | 51 | Leader |
| EXP-At.GSP579.nno + At.GSI102.nno: 3 | 22 | 810 | EXP: P-At.GSP579.nno: 2 (SEQ ID NO: 20), L-At.GSP579.nno: 1 (SEQ ID NO: 21), I-At.GSI102.nno: 1 (SEQ ID NO: 11) |
| EXP-At.GSP571.nno + At.GSP442.nno + At.Cyco: 1 | 23 | 1350 | EXP: E-At.GSP571.nno: 1 (SEQ ID NO: 24), P-At.GSP442.nno: 2 (SEQ ID NO: 2), L-At.GSP442.nno: 1 (SEQ ID NO: 3), L-At.Cyco-1: 1:2 (SEQ ID NO: 40), I-At.Cyco: 2 (SEQ ID NO: 33) |
| E-At.GSP571.nno: 1 | 24 | 422 | Enhancer |
| P-At.GSP571/442 | 25 | 902 | Chimeric Promoter: E-At.GSP571.nno: 1 (SEQ ID NO: 24), P-At.GSP442.nno: 2 (SEQ ID NO: 2) |
| EXP-At.GSP576.nno + At.GSI17.nno: 3 | 26 | 800 | EXP: P-At.GSP576.nno: 4 (SEQ ID NO: 27), L-At.GSP576.nno: 2 (SEQ ID NO: 28), I-At.GSI17.nno: 1 (SEQ ID NO: 17) |
| P-At.GSP576.nno: 4 | 27 | 458 | Promoter |
| L-At.GSP576.nno: 2 | 28 | 42 | Leader |
| T-Zm.GST59.nno: 1 | 29 | 400 | 3' UTR |
| EXP-At.GSP221 + At.Cyco: 3 | 30 | 947 | EXP: P-At.GSP221: 3 (SEQ ID NO: 31), L-At.GSP221: 1 (SEQ ID NO: 32), I-At.Cyco: 2 (SEQ ID NO: 33) |
| P-At.GSP221: 3 | 31 | 370 | Promoter |
| L-At.GSP221: 1 | 32 | 229 | Leader |
| EXP-At.GSP442 + L-I-At.Cyco | 43 | 928 | EXP: P-At.GSP442.nno: 2 (SEQ ID NO: 2), L-At.GSP442.nno: 1 (SEQ ID NO: 3), L-At.Cyco-1: 1:2 (SEQ ID NO: 40), I-At.Cyco: 2 (SEQ ID NO: 33) |
| T-Zm.GST7.nno: 2 | 44 | 300 | 3' UTR |
| EXP-At.GSP576.nno + At.Cyco: 1 | 45 | 855 | EXP: P-At.GSP576.nno: 4 (SEQ ID NO: 27), L-At.GSP576.nno: 2 (SEQ ID NO: 28), I-At.Cyco: 2 (SEQ ID NO: 33) |

Example 2

Analysis of the Synthetic EXPs, EXP-At.GSP442.nno+At.Cyco:3 and EXP-At.GSP221+At.Cyco:3, Driving GUS Expression in Stably Transformed Soybean Plants Soybean plants were transformed with vectors, specifically plant expression vectors containing regulatory element groups driving expression of the β-glucuronidase (GUS) transgene. The resulting plants were analyzed for GUS protein expression to assess the effect of the selected regulatory element groups on expression.

Soybean plants were transformed with plant GUS expression constructs comprising the endogenous EXP, EXP-At.Cyco:1:1 (SEQ ID NO:38), and two synthetic EXPs, EXP-At.GSP442.nno+At.Cyco:3 (SEQ ID NO:1) and EXP-At.GSP221+At.Cyco:3 (SEQ ID NO:30). EXP-At.Cyco:1:1 (SEQ ID NO:38) is derived from a Cytochrome c oxidase subunit VIa gene from Arabidopsis and is comprised of the promoter, P-At.Cyco-1:1:2 (SEQ ID NO:39), operably linked 5' to the leader, L-At.Cyco-1:1:2 (SEQ ID NO:40), which is operably linked 5' to an intron, I-At.Cyco-1:1:1 (SEQ ID NO:41). EXP-At.GSP442.nno+At.Cyco:3 (SEQ ID NO:1) and EXP-At.GSP221+At.Cyco:3 (SEQ ID NO:30) each comprised a synthetic promoter and leader operably linked 5' to the intron, I-At.Cyco:2 (SEQ ID NO:33). The sequence of I-At.Cyco:2 (SEQ ID NO:33) is identical to the sequence of I-At.Cyco-1:1:1 (SEQ ID NO:41), with the exception that there are two nucleotides after the intron splice site included in the sequence of I-At.Cyco-1:1:1. Both I-At.Cyco introns splice the same.

The regulatory elements were cloned into base plant expression vectors using standard methods known in the art. The resulting plant expression vectors contained a right border region from Agrobacterium tumefaciens (B-AGR-tu.right border), a first transgene selection cassette used for selection of transformed plant cells that confers resistance to the antibiotic, spectinomycin; a second transgene cassette to assess the activity of the regulatory element, which comprised an EXP sequence operably linked 5' to a coding sequence for β-glucuronidase (GUS, GOI-Ec.uidA+St.LS1: 1:1, SEQ ID NO:42) containing a processable intron derived from the potato light-inducible tissue-specific ST-LS1 gene (Genbank Accession: X04753), operably linked 5' to a 3' UTR from the Gossypium barbadense FbLate-2 gene (T-Gb.

FbL2:1, SEQ ID NO:36); and a left border region from *Agrobacterium tumefaciens* (B-AGRtu.left border).

Soybean plant cells were transformed by *Agrobacterium*-mediated transformation using these binary transformation vector constructs, as is well known in the art. The resulting transformed plant cells were induced to form whole soybean plants.

Histochemical GUS analysis was used for qualitative and quantitative expression analysis of the transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues.

For quantitative analysis of GUS expression, total protein was extracted from selected tissues of transformed soybean plants. One microgram of total protein was used with the fluorogenic substrate 4-methyleumbelliferyl-$\beta$-D-glucuronide (MUG) in a total reaction volume of 50 microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 with Micromax Reader, with slit width set at excitation 2 nm and emission 3 nm. Values are provided in units of nmol GUS/hour/mg total protein.

The following tissues were sampled for GUS expression in the $R_0$ generation; V5 stage root, leaf-sink, and source-leaf; R1 stage root, leaf-petiole, leaf-source, and flowers; R3 stage seed-immature and pod; R5 stage seed-cotyledon; and R8 stage seed-embryo and seed-cotyledon. Table 2 shows the mean quantitative GUS expression for each of the sampled tissues driven by the tested EXP regulatory element groups wherein "ND" indicates the expression in a particular tissue was not determined.

As can be seen in Table 2, each of the synthetic regulatory element groups has a unique pattern of expression in the tissues sampled compared to the endogenous EXP. For example, the synthetic At.GSP442 promoter, P-At.GSP442.nno:2 (SEQ ID NO:2), and leader, L-At.GSP442.nno:1 (SEQ ID NO:3), of EXP-At.GSP442.nno+At.Cyco:3 (SEQ ID NO:1) provides greater levels of GUS expression in all of the assayed organs relative to the endogenous EXP-At.Cyco:1:1 (SEQ ID NO:38), which comprises an identical intron sequence. Analysis of the TSS demonstrated a consistent TSS. The intron was properly excised in the resulting mRNA as expected. Further, the synthetic At.GSP221 promoter, P-AT.GSP221:3 (SEQ ID NO:31), and leader, L-At.GSP221:1 (SEQ ID NO:32), of EXP-At.GSP221+At.Cyco:3 (SEQ ID NO:30) also provides higher levels of constitutive expression in most organs assayed relative to the endogenous EXP-At.Cyco:1:1, and demonstrates a consistent TSS. However, the TSS of EXP-At.GSP221+At.Cyco:3 was not located in the predicted location—there were multiple potential TATA elements. This creates potential concerns for multiple transcripts, which could produce multiple coding sequences. As such, EXP-At.GSP221+At.Cyco:3 was not considered acceptable for use in driving transgene expression in stably transformed dicot plants. This demonstrates one of the complexities in designing synthetic expression elements. Numerous synthetic elements were assayed in the development and identification of synthetic expression elements, but only a small subset provided desirable characteristics and regulatory activity, illustrating the complexity in designing effective synthetic transcriptional regulatory elements.

As can be seen in Table 2, the synthetic promoter, P-At.GSP442.nno:2 (SEQ ID NO:2) and L-At.GSP442.nno:1 (SEQ ID NO:3) comprised within EXP-At.GSP442.nno+At.Cyco:3 (SEQ ID NO:1) is able to drive constitutive transgene expression of an operably linked transgene in a stably transformed soybean plant.

TABLE 2

Mean quantitative GUS expression in stably transformed soybean plants driven by synthetic regulatory element groups and the endogenous EXP, EXP-At.Cyco: 1:1.

| Developmental Stage | Organ | EXP-At.Cyco: 1:1 (SEQ ID NO: 38) | EXP-At.GSP442.nno + At.Cyco: 3 (SEQ ID NO: 1) | EXP-At.GSP221 + At.Cyco: 3 (SEQ ID NO: 30) |
|---|---|---|---|---|
| V5 | Root | 151 | 399 | 928 |
|  | Leaf-Sink | 39 | 65 | 59 |
|  | Leaf-Source | 52 | 109 | 100 |
| R1 | Root | ND | 616 | 1893 |
|  | Leaf-Petiole | 97 | 470 | 136 |
|  | Leaf-Source | 46 | 177 | 240 |
|  | Flowers | 71 | 277 | 140 |
| R3 | Seed-Immature | 64 | 477 | ND |
|  | Pod | 84 | 575 | 702 |
| R5 | Seed-Cotyledon | 91 | 564 | 58 |
| R8 | Seed-Embryo | 57 | 149 | 301 |
|  | Seed-Cotyledon | 100 | 1118 | 414 |

Example 3

Analysis of the Synthetic At.GSP571 Promoter and Leader, and the Synthetic At.GSI21 and At.GSI102 Introns, Driving GUS Expression in Stably Transformed Soybean Plants Soybean plants were transformed with vectors, specifically plant expression vectors containing regulatory element groups driving expression of the β-glucuronidase (GUS) transgene. The resulting plants were analyzed for GUS protein expression to assess the effect of the selected regulatory element groups on expression.

Soybean plants were transformed with plant GUS expression constructs, comprising the synthetic EXPs, EXP-At.GSP571 (SEQ ID NO:4), EXP-At.GSP571.nno+At.Cyco:2 (SEQ ID NO:7), EXP-At.GSP571.nno+At.GSI21.nno:10 (SEQ ID NO:8), and EXP-At.GSP571.nno+At.GSI102.nno:1 (SEQ ID NO:10). Each of the synthetic EXPs comprised the synthetic At.GSP571 promoter (SEQ ID NO:5) and leader (SEQ ID NO:6). EXP-At.GSP571.nno+At.Cyco:2 comprised the endogenous Arabidopsis intron, I-At.Cyco:2 (SEQ ID NO:33). EXP-At.GSP571.nno+At.GSI21.nno:10 and EXP-At.GSP571.nno+At.GSI102.nno:1 comprised the synthetic introns, I-At.GSI21.nno:2 (SEQ ID NO:9) and I-At.GSI102.nno:1 (SEQ ID NO:11), respectively. The binary plant transformation vectors were similar to those described in Example 2 with the exception that each of the At.GSP571 EXP vectors comprised the 3' UTR, T-Mt.Sali3-2-1:2:1 (SEQ ID NO:34), derived from the Sali3 gene of *Medicago truncatula*.

Quantitative and qualitative GUS expression analysis was performed as described in Example 2. Tissue samples used for analysis were the same as that described in Example 2. Table 3 shows the mean quantitative GUS expression for each of the sampled tissues driven by the tested synthetic EXP regulatory elements, wherein "ND" indicates the expression in a particular tissue was not determined.

many of the organs, providing a means to "fine-tune" the constitutive expression. Differences in expression were observed when operably linking the synthetic introns, I-At.GSI21.nno:2 (SEQ ID NO:9) and I-At.GSI102.nno:1 (SEQ ID NO:11). The synthetic introns enhanced expression in some tissues, but differed in the level of enhancement for each organ. For example, enhancement using the synthetic intron I-At.GSI21.nno:2 in R3 pod was higher than the enhancement seen using the synthetic intron I-At.GSI102.nno:1 and the endogenous intron I-At.Cyco:2 relative to EXP-At.GSP571. Expression was only slightly enhanced by the three operably linked introns in R1 petiole. In R1 flowers, I-At.GSI21.nno:2 and I-At.Cyco:2 enhanced expression, with I-At.GSI21.nno:2 providing a high level of expression enhancement and I-At.Cyco:2 providing a moderate level of enhancement. Interestingly, I-At.GSI102.nno:1 reduced expression in R1 flowers.

Analysis of the resulting mRNAs showed proper and consistent processing of the intron elements.

The synthetic promoter, P-At.GSP571.nno:5 (SEQ ID NO:5) and leader L-At.GSP571.nno:1 (SEQ ID NO:6) comprised within EXP-At.GSP571 (SEQ ID NO:4) provide constitutive expression of an operably linked transgene in stably transformed soybean plants. The synthetic EXPs, EXP-At.GSP571.nno+At.Cyco:2 (SEQ ID NO:7), which comprises the *Arabidopsis* intron I-At.Cyco:2 (SEQ ID NO:33), and EXP-At.GSP571.nno+At.GSI21.nno:10 (SEQ ID NO:8) and EXP-At.GSP571.nno+At.GSI102.nno:1 (SEQ ID NO:10), which comprise the synthetic introns I-At.GSI21.nno:2 (SEQ ID NO:9) and I-At.GSI102.nno:1 (SEQ ID NO:11), respectively, provide unique patterns of constitutive expression in stably transformed soybean plants. The synthetic introns, I-At.GSI21.nno:2 (SEQ ID NO:9) and I-At.GSI102.nno:1 (SEQ ID NO:11), provide enhanced or modulated expression in many of the plant

TABLE 3

Mean quantitative GUS expression in stably transformed soybean plants driven by synthetic regulatory elements.

| Developmental Stage | Organ | EXP-At.GSP571 (SEQ ID NO: 4) | EXP-At.GSP571.nno + At.Cyco: 2 (SEQ ID NO: 7) | EXP-At.GSP571.nno + At.GSI21.nno: 10 (SEQ ID NO: 8) | EXP-At.GSP571.nno + At.GSI102.nno: 1 (SEQ ID NO: 10) |
|---|---|---|---|---|---|
| V5 | Root | 40 | 57 | 165 | 579 |
|  | Leaf-Sink | 650 | 612 | 792 | 1683 |
|  | Leaf-Source | 1379 | 1090 | 1475 | 2128 |
| R1 | Root | 110 | ND | 457 | 645 |
|  | Leaf-Petiole | 951 | 1091 | 1267 | 1167 |
|  | Leaf-Source | 1995 | 3538 | 2094 | 2129 |
|  | Flowers | 703 | 830 | 1408 | 350 |
| R3 | Seed-Immature | 75 | 609 | 495 | 232 |
|  | Pod | 852 | 2228 | 4014 | 1535 |
| R5 | Seed-Cotyledon | 650 | 474 | 540 | 1433 |
| R8 | Seed-Embryo | 1153 | 1004 | 603 | 1122 |
|  | Seed-Cotyledon | 2449 | 4524 | 2533 | 2648 |

As can be seen in Table 3, the synthetic At.GSP571 promoter and leader provide constitutive expression in all the organs assayed. Expression was highest in the leaf and seeds. Analysis of the TSS demonstrated a consistent TSS. Operably linking an intron sequence altered expression in organs when operably linked to EXP-At.GSP571 (SEQ ID NO:4). These unique expression patterns can be used to drive specific transgenes in which the specific expression pattern of one of the four At.GSP571 EXPs is most desirable.

Example 4

Analysis of the Synthetic At.GSP564 Promoter and Leader, and the Synthetic At.GSI17 and At.GSI102 Introns, Driving GUS Expression in Stably Transformed Soybean Plants Soybean plants were transformed with vectors, specifically plant expression vectors containing regulatory element groups driving expression of the β-glucuronidase (GUS) transgene. The resulting plants were analyzed for GUS protein expression to assess the effect of the selected regulatory element groups on expression.

Soybean plants were transformed with plant GUS expression constructs, comprising the synthetic EXPs, EXP-At.GSP564 (SEQ ID NO:12), EXP-At.GSP564.nno+At.Cyco:2 (SEQ ID NO:15), EXP-At.GSP564.nno+At.GSI17.nno:2 (SEQ ID NO:16), and EXP-At.GSP564.nno+At.GSI102.nno:1 (SEQ ID NO:18). Each of the synthetic EXPs comprised the synthetic P-At.GSP564.nno:3 promoter (SEQ ID NO:13) and synthetic L-At.GSP564.nno.1 leader (SEQ ID NO:14). EXP-At.GSP564.nno+At.Cyco:2 comprised the *Arabidopsis* intron, I-At.Cyco:2 (SEQ ID NO:33). EXP-At.GSP564.nno+At.GSI17.nno:2 and EXP-At.GSP564.nno+At.GSI102.nno:1 comprised the synthetic introns, I-At.GSI17.nno:1 (SEQ ID NO:17) and I-At.GSI102.nno:1 (SEQ ID NO:11), respectively. The binary plant transformation vectors were similar to those described in Example 2, with the exception that each of the At.GSP564 EXP vectors comprised the 3' UTR, T-Mt.Oxr-1:2:1 (SEQ ID NO:35), derived from a putative oxidoreductase (OXR) protein gene from *Medicago truncatula*.

Quantitative and qualitative GUS expression analysis was performed as described in Example 2. Tissue samples used for analysis were the same as that described in Example 2. Table 4 shows the mean quantitative GUS expression for each of the sampled tissues driven by the tested synthetic EXP regulatory elements, wherein "ND" indicates the expression in a particular tissue was not determined.

seeds. Analysis of the TSS demonstrated a consistent TSS. Operably linking an intron sequence altered expression in many of the organs, providing a means to "fine-tune" the constitutive expression. Differences in expression were observed when operably linking the synthetic introns, I-At.GSI17.nno:1 (SEQ ID NO:17) and I-At.GSI102.nno:1 (SEQ ID NO:11). The synthetic introns enhanced expression in some tissues relative to EXP-At.GSP564, but differed in the level of enhancement for each organ. For example, enhancement using the synthetic intron I-At.GSI102.nno:1 in V5 source leaf was higher than the enhancement seen using the synthetic intron I-At.GSI17.nno:1. In R1 root, enhancement using the synthetic intron I-At.GSI17.nno:1 was higher than the enhancement conferred by the synthetic intron I-At.GSI102.nno:1. Both synthetic introns provided greater enhancement of expression in R1 source leaf than the endogenous intron, I-At.Cyco:2.

Analysis of the resulting mRNAs showed proper and consistent processing of the intron elements.

The synthetic At.GSP564 promoter, P-At.GSP564.nno:3 (SEQ ID NO:13) and leader, L-At.GSP564.nno:1 (SEQ ID NO:14) comprising EXP-At.GSP564 (SEQ ID NO:12) provide constitutive expression of an operably linked transgene in stably transformed soybean plants. The synthetic EXPs, EXP-At.GSP564.nno+At.Cyco:2 (SEQ ID NO:15), which comprises the *Arabidopsis* intron I-At.Cyco:2 (SEQ ID NO:33), and EXP-At.GSP564.nno+At.GSI17.nno:2 (SEQ ID NO:16) and EXP-At.GSP564.nno+At.GSI102.nno:1 (SEQ ID NO:18), which comprise the synthetic introns, I-At.GSI17.nno:1 (SEQ ID NO:17) and I-At.GSI102.nno:1 (SEQ ID NO:11), respectively, provide unique patterns of constitutive expression in stably transformed soybean plants. The synthetic introns, I-At.GSI17.nno:1 (SEQ ID NO:17) and I-At.GSI102.nno:1 (SEQ ID NO:11), provide enhanced or modulated transgene expression in many of the plant organs when operably linked to EXP-At.GSP564 (SEQ ID NO:12). These unique expression patterns can be

TABLE 4

Mean quantitative GUS expression in stably transformed soybean plants driven by synthetic regulatory elements.

| Developmental Stage | Organ | EXP-At.GSP564 (SEQ ID NO: 12) | EXP-At.GSP564.nno + At.Cyco: 2 (SEQ ID NO: 15) | EXP-At.GSP564.nno + At.GSI17.nno: 2 (SEQ ID NO: 16) | EXP-At.GSP564.nno + At.GSI102.nno: 1 (SEQ ID NO: 18) |
|---|---|---|---|---|---|
| V5 | Root | 61 | 108 | 54 | 145 |
|  | Leaf-Sink | 38 | 220 | 89 | 259 |
|  | Leaf-Source | 74 | 421 | 209 | 1229 |
| R1 | Root | 118 | 165 | 2348 | 627 |
|  | Leaf-Petiole | 90 | 235 | 273 | 148 |
|  | Leaf-Source | 140 | 205 | 436 | 917 |
|  | Flowers | 66 | 91 | ND | 305 |
| R3 | Seed-Immature | 26 | ND | 101 | ND |
|  | Pod | 40 | ND | 749 | ND |
| R5 | Seed-Cotyledon | 25 | 88 | 78 | 61 |
| R8 | Seed-Embryo | 38 | 97 | 137 | 70 |
|  | Seed-Cotyledon | 79 | 288 | 655 | 572 |

As can be seen in Table 4, the synthetic At.GSP564 promoter and leader provide constitutive expression in all the organs assayed. Expression was highest in the leaf and used to drive specific transgenes in which the specific expression pattern of one of the four At.GS564 EXPs is most desirable.

Example 5

Analysis of the Synthetic EXP, EXP-At.GSP579.nno+At.GSI102.nno:3, Driving GUS Expression in Stably Transformed Soybean Plants Soybean plants were transformed with vectors, specifically plant expression vectors containing a synthetic regulatory element group driving expression of the β-glucuronidase (GUS) transgene. The resulting plants were analyzed for GUS protein expression to assess the effect of the selected synthetic regulatory element group on expression.

Soybean plants were transformed with a plant GUS expression construct, comprising the synthetic EXP, EXP-At.GSP579.nno+At.GSI102.nno:3 (SEQ ID NO:22). EXP-At.GSP579.nno+At.GSI102.nno:3 comprises EXP-At.GSP579 (SEQ ID NO:19) consisting of the At.GSP-At.GSP579 promoter and leader (SEQ ID NOs:20 and 21, respectively), operably linked 5' to the synthetic intron, I-At.GSI102.nno:1 (SEQ ID NO:11). The GUS transgene cassette also comprises the 3' UTR, T-Mt.RD22-1:2:1 (SEQ ID NO:37) derived from a dehydration-responsive protein RD22 gene from *Medicago truncatula*.

Quantitative and qualitative GUS expression analysis was performed as described in Example 2. Tissue samples used for analysis were the same as that described in Example 2. Table 5 shows the mean quantitative GUS expression for each of the sampled tissues driven by the synthetic EXP, EXP-At.GSP579.nno+At.GSI102.nno:3, wherein "ND" indicates the expression in a particular tissue was not determined.

TABLE 5

Mean quantitative GUS expression in stably transformed soybean plants driven by EXP-At.GSP579.nno + At.GSI102.nno: 3.

| Developmental Stage | Organ | EXP-At.GSP579.nno + At.GSI102.nno: 3 (SEQ ID NO: 22) |
| --- | --- | --- |
| V5 | Root | 187 |
|  | Leaf-Sink | 311 |
|  | Leaf-Source | 458 |
| R1 | Root | 148 |
|  | Leaf-Petiole | 118 |
|  | Leaf-Source | 425 |
|  | Flowers | 130 |
| R3 | Seed-Immature | ND |
|  | Pod | ND |
| R5 | Seed-Cotyledon | ND |
| R8 | Seed-Embryo | 127 |
|  | Seed-Cotyledon | 266 |

As can be seen in Table 5, EXP-At.GSP579.nno+At.GSI102.nno:3 (SEQ ID NO:22) provides constitutive expression in stably transformed soybean plants. The synthetic promoter P-At.GSP579.nno:2 (SEQ ID NO:20) and leader L-At.GSP579.nno:1 (SEQ ID NO:21) comprised within EXP-At.GSP579 (SEQ ID NO:19) drive constitutive expression of an operably linked transgene. It can be inferred by the previous Examples in which the synthetic intron, I-At.GSI102.nno:1 (SEQ ID NO:11), was operably linked to other constitutive synthetic promoters that I-At.GSI102.nno:1 enhanced or modulated the constitutive expression imparted by EXP-At.GSP579 in at least some of the organs sampled.

Example 6

Analysis of the Synthetic EXP, EXP-At.GSP571.nno+At.Cyco:2, Driving GUS Expression in Stably Transformed Cotton Plants Cotton plants were transformed with a vector, specifically a plant expression vector containing a synthetic regulatory element group driving expression of the β-glucuronidase (GUS) transgene. The resulting plants were analyzed for GUS protein expression to assess the effect of the synthetic regulatory element group on expression.

A plant binary vector comprising the synthetic EXP, EXP-At.GSP571.nno+At.Cyco:2 (SEQ ID NO:7), similar to that described in Example 3, was used to stably transform cotton plants. The GUS transgene cassette comprised EXP-At.GSP571.nno+At.Cyco:2 operably linked 5' to a coding sequence for β-glucuronidase (GUS, GOI-Ec.uidA+St.LS1:1:1, SEQ ID NO:42) containing a processable intron derived from the potato light-inducible tissue-specific ST-LS1 gene (Genbank Accession: X04753), operably linked 5' to a 3' UTR from the *Gossypium barbadense* FbLate-2 gene (T-Gb.FbL2:1, SEQ ID NO:36). The resulting transformed cotton events were grown and tissue samples were derived from 4Node Leaf; 8Node Petiole, Sink Leaf, and Source Leaf; Pre-fertilization Square Bracts and Square Bud; Flowering Anther and Flower Ovary; and 8 Days After Pollination (DAP) Boll Wall were sampled and assayed for qualitative and quantitative GUS expression.

Table 6 shows the mean quantitative GUS expression for each of the sampled tissues driven by the synthetic EXP, EXP-At.GSP571.nno+At.Cyco:2.

TABLE 6

Mean quantitative GUS expression in stably transformed cotton plants driven by EXP-At.GSP571.nno + At.Cyco: 2.

| Stage | Organ | Mean |
| --- | --- | --- |
| 4Node | Leaf | 1232.57 |
| 8Node | Leaf, Petiole | 223.68 |
|  | Leaf, Sink | 612.14 |
|  | Leaf, Source | 618.9 |
| Pre-fertilization | Square Bracts | 381.69 |
|  | Square Bud | 347.22 |
| Flowering | Anther | 64.66 |
|  | Flower, Ovary | 210.92 |
| 8DAP | Boll Wall | 835.94 |

As can be seen in Table 6, EXP-At.GSP571.nno+At.Cyco:2 expressed in all the tissues sampled. Expression was highest in 4Node Leaf and lowest in the Flowering Anther. Expression in 8Node Sink and Source Leaf were relatively the same and about half that of the 4Node Leaf. Expression was also high in the Boll Wall. Table 6 demonstrates that the promoter, P-At.GSP571.nno:5 (SEQ ID NO:5), is able to drive constitutive expression in stably transformed cotton plants. The intron, I-At.Cyco:2 (SEQ ID NO:33), within EXP-At.GSP571.nno+At.Cyco:2 enhanced expression of the P-At.GSP571.nno:5 promoter in stably transformed soybean plants, as shown in Example 3.

Example 7

Analysis of the Synthetic Chimeric Promoter P-At.GSP571/442 Driving GUS Expression in Stably Transformed Soybean Plants Soybean plants were transformed with vectors, specifically plant expression vectors containing regulatory element groups driving expression of the β-glucuronidase (GUS) transgene. The resulting plants were analyzed for GUS protein expression to assess the effect of the selected synthetic regulatory element groups on expression.

Soybean plants were transformed with a plant binary vector comprising the synthetic EXP, EXP-At.GSP571.nno+At.GSP442.nno+At.Cyco:1 (SEQ ID NO:23), which is comprised of the synthetic chimeric promoter P-At.GSP571/442 (SEQ ID NO:25) comprising a synthetic enhancer E-At.GSP571.nno:1 (SEQ ID NO:24) derived from the synthetic promoter P-At.GSP571.nno:5 (SEQ ID NO:5) which is operably linked 5' to the synthetic promoter P-At.GSP442.nno:2 (SEQ ID NO:2) and is operably linked 5' with the synthetic leader, L-At.GSP442.nno:1 (SEQ ID NO:3), operably linked 5' to the leader, L-At.Cyco-1:1:2 (SEQ ID NO:40), which is operably linked 5' to the intron, I-At.Cyco:2 (SEQ ID NO:33). The GUS transgene cassette comprised EXP-At.GSP571.nno+At.GSP442.nno+At.Cyco:1 operably linked 5' to a coding sequence for β-glucuronidase (GUS, GOI-Ec.uidA+St.LS1:1:1, SEQ ID NO:42) containing a processable intron derived from the potato light-inducible tissue-specific ST-LS1 gene (Genbank Accession: X04753), operably linked 5' to the synthetic 3' UTR, T-Zm.GST59.nno:1 (SEQ ID NO:29).

A plant binary vector used to compare the activity of the chimeric promoter was also constructed. The vector comprised an EXP, EXP-At.GSP442+L-I-At.Cyco (SEQ ID NO:43), which is comprised of the synthetic promoter, P-At.GSP442.nno:2 (SEQ ID NO:2), operably linked 5' to the synthetic leader, L-At.GSP442.nno:1 (SEQ ID NO:3), operably linked 5' to the leader, L-At.Cyco-1:1:2 (SEQ ID NO:40), which is operably linked 5' to the intron, I-At.Cyco:2 (SEQ ID NO:33). The binary vectors are similar to those described in Examples 2-6, with the exception that each GUS transgene cassette has the synthetic 3' UTR, T-Zm.GST59.nno:1 (SEQ ID NO:29) operably linked 3' to the GUS coding sequence.

Soybean plants were transformed with the two binary vectors. Tissue samples were taken of selected organs at specific developmental stages and assayed for qualitative and quantitative GUS expression. Table 7 shows the mean quantitative GUS expression for each of the sampled tissues driven by the synthetic EXPs, EXP-At.GSP571.nno+At.GSP442.nno+At.Cyco:1 and EXP-At.GSP442+L-I-At.Cyco.

TABLE 7

Mean quantitative GUS expression in stably transformed soybean plants driven by EXP-At.GSP571.nno + At.GSP442.nno + At.Cyco: 1 and EXP-At.GSP442 + L-I-At.Cyco.

| Stage | Organ | EXP-At.GSP442 + L-I-At.Cyco (SEQ ID NO: 43) Mean | EXP-At.GSP571.nno + At.GSP442.nno + At.Cyco: 1 (SEQ ID NO: 23) Mean |
|---|---|---|---|
| V5 | Leaf, Sink | 69.61 | 72.12 |
|  | Leaf, Source | 88.22 | 96.06 |
|  | Root | 74.67 | 102.9 |
| R1 | Flowers | 79.16 | 62.01 |
|  | Leaf, Petiole | 77.07 | 87 |
|  | Leaf, Source | 66.59 | 114.33 |
|  | Root | 76.88 | 123.12 |
| R3 | Pod | 93.19 | 102.54 |
|  | Seed, Immature | 71.15 | 61.62 |
| R5 | Seed, Cotyledon | 78.72 | 92.83 |
| R8 | Seed, Cotyledon | 65.55 | 72.15 |
|  | Seed, Embryo | 129.95 | 107.66 |

As can be seen in Table 7, the addition of the synthetic enhancer E-At.GSP571.nno:1 enhanced expression in many of the tissues sampled. Both EXPs provided constitutive expression in the stably transformed soybean plants. The synthetic 3' UTR, T-Zm.GST59.nno:1, functioned in a similar manner as a native 3' UTR in providing proper termination and polyadenylation of the transcript.

Example 8

Analysis of the Synthetic Chimeric Promoter P-At.GSP571/442 Driving GUS Expression in Stably Transformed Cotton Plants Cotton plants were transformed with a vector, specifically a plant expression vector containing a synthetic regulatory element group driving expression of the β-glucuronidase (GUS) transgene. The resulting plants were analyzed for GUS protein expression to assess the effect of the selected synthetic regulatory element group on expression.

Cotton plants were transformed with a plant binary vector comprising the synthetic EXP, EXP-At.GSP571.nno+At.GSP442.nno+At.Cyco:1 (SEQ ID NO:23), which is comprised of the synthetic chimeric promoter P-At.GSP571/442 (SEQ ID NO:25) comprising a synthetic enhancer E-At.GSP571.nno:1 (SEQ ID NO:24) derived from the synthetic promoter P-At.GSP571.nno:5 (SEQ ID NO:5) which is operably linked 5' to the synthetic promoter P-At.GSP442.nno:2 (SEQ ID NO:2) and is operably linked 5' to the synthetic leader, L-At.GSP442.nno:1 (SEQ ID NO:3), operably linked 5' to the leader, L-At.Cyco-1:1:2 (SEQ ID NO:40), which is operably linked 5' to the intron, I-At.Cyco:2 (SEQ ID NO:33). The GUS transgene cassette comprised EXP-At.GSP571.nno+At.GSP442.nno+At.Cyco:1 operably linked 5' to a coding sequence for β-glucuronidase (GUS, GOI-Ec.uidA+St.LS1:1:1, SEQ ID NO:42) containing a processable intron derived from the potato light-inducible tissue-specific ST-LS1 gene (Genbank Accession: X04753), operably linked 5' to the synthetic 3' UTR, T-Zm.GST59.nno:1 (SEQ ID NO:29). The resulting transformed cotton events were grown and tissue samples derived from 4Node Leaf; 8Node Petiole, Sink Leaf, and Source Leaf; Pre-fertilization Square Bracts and Square Bud; Flowering Anther and Flower Ovary; and 8 Days After Pollination (DAP) Boll Wall were sampled and assayed for qualitative and quantitative GUS expression.

Table 8 shows the mean quantitative GUS expression for each of the sampled tissues driven by the synthetic EXP, EXP-At.GSP571.nno+At.GSP442.nno+At.Cyco:1 wherein "bdl" means below detection limit.

TABLE 8

Mean quantitative GUS expression in stably transformed cotton plants driven by EXP-At.GSP571.nno + At.GSP442.nno + At.Cyco: 1.

| Stage | Organ | Mean |
| --- | --- | --- |
| 4Node | Leaf | 177.74 |
| 8Node | Leaf, Petiole | bdl |
|  | Leaf, Sink | 108.39 |
|  | Leaf, Source | 294.99 |
| Pre-fertilization | Square Bracts | 78.84 |
|  | Square Bud | 118.21 |
| Flowering | Anther | 69.19 |
|  | Flower, Ovary | 69.78 |
| 8DAP | Boll Wall | 159.58 |

As can be seen in Table 8, EXP-At.GSP571.nno+At.GSP442.nno+At.Cyco:1 (SEQ ID NO:23) was able to drive constitutive GUS expression in the tissues sampled. Expression in the Petiole was determined to be below detection limits. Expression was highest in 8Node Source Leaf. Expression was relatively equal in the Flowering Anther and Flower Ovary. In addition, the synthetic 3' UTR, T-Zm.GST59.nno:1 (SEQ ID NO:29) functioned in a similar manner as a native 3' UTR in providing proper termination and polyadenylation of the transcript.

Example 9

Analysis of the Synthetic EXP, EXP-At.GSP576.nno+At.Cyco:1, Driving GUS Expression in Stably Transformed Soybean Plants Soybean plants were transformed with a vector, specifically a plant expression vector containing a synthetic regulatory element group driving expression of the β-glucuronidase (GUS) transgene. The resulting plants were analyzed for GUS protein expression to assess the effect of the selected synthetic regulatory element group on expression.

Soybean plants were transformed with a plant binary vector comprising the synthetic EXP, EXP-At.GSP576.nno+At.Cyco:1 (SEQ ID NO:45). The GUS transgene cassette also comprised the 3' UTR from the Gossypium barbadense FbLate-2 gene (T-Gb.FbL2:1, SEQ ID NO:36), operably linked 3' to the GUS coding sequence. The resulting transformed soybean events were grown and tissue samples of selected organs from several developmental stages were sampled and assayed for qualitative and quantitative GUS expression. Expression of GUS in the stably transformed soybean plants, driven by EXP-At.GSP576.nno+At.Cyco:1, is presented in Table 9.

TABLE 9

Mean quantitative GUS expression in stably transformed soybean plants driven by EXP-At.GSP576.nno + At.Cyco: 1.

| Developmental Stage | Organ | Mean |
| --- | --- | --- |
| V5 | Root | 60.95 |
|  | Leaf-Sink | 97.43 |
|  | Leaf-Source | 181.64 |
| R1 | Root | 82.4 |
|  | Leaf-Petiole | 208.28 |
|  | Leaf-Source | 214 |
|  | Flowers | 123.37 |
| R3 | Seed-Immature | 95.29 |
|  | Pod | 158.24 |
| R5 | Seed-Cotyledon | 85.97 |
| R8 | Seed-Embryo | 67.4 |
|  | Seed-Cotyledon | 52.92 |

As can be seen in Table 9, EXP-At.GSP576.nno+At.Cyco:1 (SEQ ID NO:45) provided constitutive expression in stably transformed soybean plants. The synthetic promoter P-At.GSP576.nno:4 (SEQ ID NO:27) and leader L-At.GSP576.nno:2 (SEQ ID NO:28) drive constitutive expression of an operably linked transgene. It can be inferred by the previous Examples in which the intron, I-At.Cyco:2 (SEQ ID NO:33), was operably linked to other constitutive synthetic promoters, that I-At.Cyco:2 enhanced or modulated the constitutive expression imparted by P-At.GSP576.nno:4 in at least some of the organs sampled.

Example 10

Analysis of the Synthetic EXP, EXP-At.GSP576.nno+At.GSI17.nno:3, Driving GUS Expression in Stably Transformed Soybean Plants Soybean plants are transformed with vectors, specifically plant expression vectors containing regulatory element groups driving expression of the β-glucuronidase (GUS) transgene. The resulting plants are analyzed for GUS protein expression to assess the effect of the selected regulatory element groups on expression.

Soybean plants are transformed with plant binary vectors comprising either the synthetic EXP, EXP-At.GSP576.nno+At.GSI17.nno:3 (SEQ ID NO:26), or the EXP, EXP-At.Cyco:1:1 (SEQ ID NO:38). The GUS transgene cassettes also comprise the 3' UTR from the Gossypium barbadense FbLate-2 gene (T-Gb.FbL2:1, SEQ ID NO:36) operably linked 3' to the GUS coding sequence. The resulting transformed soybean events are grown and tissue samples of selected organs from several developmental stages are sampled and assayed for qualitative and quantitative GUS expression. Expression of GUS in the stably transformed soybean plants, driven by EXP-At.GSP576.nno+At.GSI17.nno:3, is compared to the expression driven by EXP-At.Cyco:1:1. Expression of GUS in stably transformed soybean plants driven by EXP-At.GSP576.nno+At.GSI17.nno:3 is demonstrative of the ability of the synthetic promoter P-At.GSP576.nno:4 (SEQ ID NO:27) and leader L-At.GSP576.nno:2 (SEQ ID NO:28) to drive constitutive expression of an operably linked transgene.

As demonstrated in Examples 9 and 11, the synthetic promoter P-At.GSP576.nno:4 (SEQ ID NO:27) and leader L-At.GSP576.nno:2 (SEQ ID NO:28) drive constitutive expression of an operably linked transgene. As was demonstrated in Example 4, the synthetic intron, I-At.GSI17.nno:1

(SEQ ID NO:17) enhanced or modulated transgene expression in many of the plant organs when operably linked to EXP-At.GSP564 (SEQ ID NO:12). Likewise, it can be reasonably expected that expression of the synthetic promoter P-At.GSP576.nno:4 and leader L-At.GSP576.nno:2 would be enhanced or modulated in a similar manner.

Example 11

Analysis of the Synthetic EXP, EXP-At.GSP576.nno+At.GSI17.nno:3, Driving GUS Expression in Stably Transformed Cotton Plants Cotton plants were transformed with a vector, specifically a plant expression vector containing a synthetic regulatory element group driving expression of the β-glucuronidase (GUS) transgene. The resulting plants were analyzed for GUS protein expression to assess the effect of the selected synthetic regulatory element group on expression.

Cotton plants were transformed with a binary vector comprising the synthetic EXP, EXP-At.GSP576.nno+At.GSI17.nno:3 (SEQ ID NO:26), as previously described in Example 10. The GUS transgene cassettes also comprised the 3' UTR from the *Gossypium barbadense* FbLate-2 gene (T-Gb.FbL2:1, SEQ ID NO:36) operably linked 3' to the GUS coding sequence. The resulting transformed cotton events were grown and tissue samples derived from 4Node Leaf; 8Node Petiole, Sink Leaf, and Source Leaf; Pre-fertilization Square Bracts and Square Bud; Flowering Anther and Flower Ovary; and 8 Days After Pollination (DAP) Boll Wall were sampled and assayed for qualitative and quantitative GUS expression.

Table 10 shows the mean quantitative GUS expression for each of the sampled tissues driven by the synthetic EXP-At.GSP576.nno+At.GSI17.nno:3.

TABLE 10

Mean quantitative GUS expression in stably transformed cotton plants driven by EXP-At.GSP576.nno + At.GSI17.nno: 3.

| Stage | Organ | Mean |
|---|---|---|
| 4Node | Leaf | 579.03 |
| 8Node | Leaf, Petiole | 301.57 |
|  | Leaf, Sink | 159.4 |
|  | Leaf, Source | 577.11 |
| Pre-fertilization | Square Bracts | 262.66 |
|  | Square Bud | 223.59 |
| Flowering | Anther | 171.2 |
|  | Flower, Ovary | 109 |
| 8DAP | Boll Wall | 433.64 |

As can be seen in Table 10, EXP-At.GSP576.nno+At.GSI17.nno:3 (SEQ ID NO: 26) drove constitutive expression of the GUS transgene in stably transformed cotton plants. Expression was highest in 4Node Leaf, 8Node Source Leaf, and 8DAP Boll Wall. The synthetic promoter P-At.GSP576.nno:4 (SEQ ID NO:27) and leader L-At.GSP576.nno:2 (SEQ ID NO:28) are able to drive constitutive expression of an operably linked transgene in stably transformed cotton plants. As was demonstrated in Example 4, the synthetic intron, I-At.GSI17.nno:1 (SEQ ID NO:17), enhanced or modulated transgene expression in many of the plant organs when operably linked to EXP-At.GSP564 (SEQ ID NO:12). Likewise, it can be reasonably expected that expression of the synthetic promoter, P-At.GSP576.nno:4 and leader, L-At.GSP576.nno:2, would be enhanced or modulated in a similar manner in stably transformed cotton plants.

Example 12

Enhancer Elements Derived from the Regulatory Element

Enhancers are derived from the promoter elements presented as SEQ ID NOs: 2, 5, 13, 20, 25, 27, 31, and 39. The enhancer element may be comprised of one or more cis regulatory elements that when operably linked 5' or 3' to a promoter element, or operably linked 5' or 3' to additional enhancer elements that are operably linked to a promoter, can enhance or modulate expression levels of a transcribable DNA molecule, or provide expression of a transcribable DNA molecule in a specific cell type or plant organ or at a particular time point in development or circadian rhythm. Enhancers are made by removing the TATA box or functionally similar elements and any downstream sequence from the promoters that allow transcription to be initiated from the promoters presented as SEQ ID NOs: 2, 5, 13, 20, 25, 27, 31, and 39 or fragments thereof. For example, the synthetic enhancer, E-At.GSP571.nno:1 (SEQ ID NO:24) was derived from the synthetic promoter, P-At.GSP571.nno:5 (SEQ ID NO:5) and consists of nucleotides 1 through 422 of P-At.GSP571.nno:5, eliminating the 3' downstream sequence which also contains the TATA box of the synthetic promoter.

Further refinement of the enhancer element may be required and is validated empirically. In addition, position of the enhancer element relative to other elements within a chimeric regulatory element group is also empirically determined, since the order of each element within the chimeric regulatory element group may impart different effects, depending upon the relative positions of each element. Some promoter elements will have multiple TATA box or TATA box-like elements and potentially multiple transcription start sites. Under those circumstances, it may be necessary to first identify where the first TSS is located and then begin designing enhancers using the first TSS to prevent the potential initiation of transcription from occurring within a putative enhancer element.

Enhancer elements, derived from the synthetic promoter elements presented as SEQ ID NOs: 2, 5, 13, 20, 25, 27, 31, and 39 are cloned using methods known in the art to be operably linked 5' or 3' to a promoter element, or operably linked 5' or 3' to additional enhancer elements that are operably linked to a promoter. Alternatively, enhancer elements can be cloned, using methods known in the art, to provide a larger enhancer element that is comprised of two or more copies of the enhancer and cloned using methods known in the art to be operably linked 5' or 3' to a promoter element, or operably linked 5' or 3' to additional enhancer elements that are operably linked to a promoter producing a chimeric transcriptional regulatory element. Enhancer elements can also be cloned using methods known in the art to be operably linked 5' to a promoter element derived from a different genus organism, or operably linked 5' or 3' to additional enhancer elements derived from other genus organisms that are operably linked to a promoter derived from either the same or different genus organism, resulting in a chimeric regulatory element. A GUS expression plant transformation vector may be constructed using methods known in the art similar to the constructs described in Example 2 in which the resulting plant expression vectors contain a right border region from *Agrobacterium tumefaciens* (B-AGRtu.right border), a first transgene selection cassette used for selection of transformed plant cells that confers resistance to the antibiotic, spectinomycin; and a second transgene cassette to test the enhancer element comprised of, the enhancer element operably linked 5' or 3' to a promoter element or operably linked 5' or 3' to additional enhancer elements that are in turn operably linked to a promoter which is operably linked 5' to a leader element, operably linked to a coding sequence for β-glucuronidase (GUS, GOI-Ec.uidA+St.LS1:1:1, SEQ ID NO:42) containing a processable intron derived from the potato light-inducible tissue-specific ST-LS1 gene (Genbank Accession: X04753), operably linked to a 3' termination region, and a left border region from *A. tumefaciens* (B-AGRtu.left border). The resulting plasmids are used to transform soybean plants or other genus plants by the methods described in the Examples. Alternatively, protoplast cells derived from soybean or other genus plants are transformed using methods known in the art to perform transient assays.

GUS expression driven by a regulatory element comprising one or more enhancers is evaluated in stable or transient plant assays to determine the effects of the enhancer element on expression of a transcribable DNA molecule. Modifications to one or more enhancer elements or duplication of one or more enhancer elements may be performed based upon empirical experimentation and the resulting gene expression regulation that is observed using each regulatory element composition. Altering the relative positions of one or more enhancers in the resulting regulatory or chimeric regulatory elements may affect the transcriptional activity or specificity of the regulatory or chimeric regulatory element and is determined empirically to identify the best enhancers for the desired transgene expression profile within the soybean plant or other genus plant.

Example 13

Analysis of the Effect Upon GUS Expression Imparted by the Synthetic 3' UTR, T-Zm.GST7.nno:2, in Stably Transformed Soybean Plants Soybean plants were transformed with a vector, specifically plant expression vectors containing regulatory element groups driving expression of the β-glucuronidase (GUS) transgene. The resulting plants were analyzed for GUS protein expression to assess the effect of selected regulatory elements on expression.

Soybean plants were transformed with two binary vectors comprising EXP-At.GSP571 (SEQ ID NO:4) driving GUS expression. The GUS transgene cassettes also comprised either the endogenous 3' UTR T-Mt.Sali3-2-1:2:1 (SEQ ID NO:34) or the synthetic 3' UTR, T-Zm.GST7.nno:2 (SEQ ID NO:44). GUS protein expression was quantitatively measured in the organs of stably transformed soybean plants transformed with the two constructs. Expression of GUS was compared between the constructs. Table 11 below shows the mean GUS expression modulated by the synthetic 3' UTR, T-Zm.GST7.nno:2, relative to the endogenous 3' UTR, T-Mt.Sali3-2-1:2:1, wherein "nd" mean not determined and "bdl" means below detection limit.

TABLE 11

Mean quantitative GUS expression in stably transformed soybean plants.

| Developmental Stage | Organ | T-Mt.Sali3-2-1: 2:1 (SEQ ID NO: 34) | T-Zm.GST7.nno: 2 (SEQ ID NO: 44) | Fold Attenuation |
|---|---|---|---|---|
| V5 | Root | 40 | bdl | |
| | Leaf-Sink | 650 | 88 | 7.4 |
| | Leaf-Source | 1379 | 278 | 5.0 |
| R1 | Root | 110 | 72 | 1.5 |
| | Leaf-Petiole | 951 | 199 | 4.8 |
| | Leaf-Source | 1995 | 642 | 3.1 |
| | Flowers | 703 | 139 | 5.1 |
| R3 | Seed-Immature Pod | 75 | bdl | |
| | | 852 | 386 | 2.2 |
| R5 | Seed-Cotyledon | 650 | 174 | 3.7 |
| R8 | Seed-Embryo | 1153 | nd | |
| | Seed-Cotyledon | 2449 | nd | |

As can be seen in Table 11, the synthetic 3' UTR, T-Zm.GST7.nno:2 attenuated expression relative to the 3' UTR, T-Mt.Sali3-2-1:2:1 in all tissues assayed. The degree of attenuation varied for each tissue from 1.5 fold in R1 Roots to 7.4 fold in V5 Sink Leaf. The use of a 3' UTR to attenuate expression in stably transformed plants has great utility. For example, a 3' UTR can be used in combination with other regulatory elements such as promoters, leaders, and introns to fine tune expression of a transgene, particularly those wherein high expression may lead to off-phenotypic effects that are deleterious to the transformed plant. Analysis of the resulting GUS transcript confirmed proper termination of the transcript imparted by the synthetic 3' UTR, T-Zm.GST7.nno:2. The synthetic 3' UTR, T-Zm.GST7.nno:2, is able to modulate expression and properly terminate transcription in stably transformed soybean plants.

Example 14

Analysis of the Synthetic 3' UTRs, T-Zm.GST7.nno:2 and T-Zm.GST59.nno:1, on GUS Expression in Corn Protoplast Cells Corn leaf protoplasts were transformed with vectors, specifically expression vectors containing test regulatory elements driving expression of the β-glucuronidase (GUS) transgene. The resulting transformed corn leaf protoplasts were analyzed for GUS protein expression to assess the effect of the selected regulatory elements on expression.

Corn protoplasts, derived from leaf tissue, were transformed with expression vectors comprising synthetic expression elements and compared to expression elements known in the art. Two expression vectors were constructed to assess the activity of the synthetic 3' UTRs, T-Zm.GST7.nno:2 (SEQ ID NO:44) and T-Zm.GST59.nno:1 (SEQ ID NO:29) and two construct expression vectors were also constructed. Each of the four constructs comprised a transgene cassette comprising the constitutive promoter and leader, EXP-CaMV.35S (SEQ ID NO:46), operably linked 5' to the intron I-Zm.DnaK:1 (SEQ ID NO:47), operably linked 5' to a GUS coding sequence, GOI-Ec.uidA+St.LS1:1:1 (SEQ ID NO:42). The expression vectors used to assess the synthetic 3' UTRs comprised either T-Zm.GST7.nno:2 or T-Zm.GST59.nno:1 operably linked 3' to the GUS coding sequence. One control vector comprised the 3' UTR T-Os.LTP:1 (SEQ ID NO:48) operably linked 3' to the GUS coding sequence. The other control vector lacked a 3' UTR.

A plasmid used in co-transformation of the protoplasts and normalization of the data was also constructed using methods known in the art. It comprised a transgene cassette comprised of, EXP-CaMV.35S (SEQ ID NO:46) operably linked 5' to a coding sequence encoding the NanoLuc® luciferase fluorescent protein (Promega, Madison, Wis. 53711), Nluc (SEQ ID NO:49), which was operably linked 5' to a 3' UTR, T-Os.LTP:1 (SEQ ID NO:48).

Corn leaf protoplasts were transformed using a PEG-based transformation method, similar to those known in the art. Protoplast cells were transformed in a ninety six well format. Twelve micrograms of the test vector DNA or control vector DNA, and six micrograms of the NanoLuc® vector DNA were used to transform $3.2 \times 10^5$ protoplasts per well. After transformation, the protoplasts were incubated at 25° C. in the dark for sixteen to twenty hours. Following incubation, the protoplasts were lysed and the lysate used for measuring luciferase and GUS expression. To lyse the cells, the cells in the plate were pelleted through centrifugation, washed, resuspended in a smaller volume, and transferred to strip well tubes. The tubes were centrifuged again and supernatant was aspirated leaving the protoplast cell pellet behind. The cell pellet was resuspended in QB buffer (100 mM $KPO_4$, pH 7.8; 1 mM EDTA; 1% Triton X-100; 10% Glycerol; 1 mM DTT). The cells were lysed by vigorously pipetting the cells several times, vortexing the tubes, and letting the tubes incubate on ice for five minutes. The lysate was then centrifuged to pellet the cell debris. The resulting lysate was then transferred to a clean plate.

Luciferase activity was assayed using the Nano-Glo® Luciferase Assay Substrate (Promega, Madison, Wis. 53711) in QB buffer. In short, a small volume of lysate, QB buffer, and the Nano-Glo® Luciferase Assay Substrate/QB solution were mixed together in white, ninety six well plates. Fluorescence was then measured using a PHERAstar® plate reader (BMG LABTECH Inc., Cary, N.C. 27513).

GUS activity was assayed using the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. An aliquot of lysate was mixed with an aliquot of MUG dissolved in QB buffer and incubated at 37° C. A small aliquot of the lysate/MUG reaction mixture was removed and added to a stop buffer at three different timepoints; (1) immediately after mixing the lysate/MUG reaction as "Time zero minutes"; (2) twenty minutes; and (3) sixty minutes. Fluorescence was measured with excitation at 355 nm, emission at 460 nm using a using a PHERAstar® plate reader (BMG LABTECH Inc., Cary, N.C. 27513).

At least two plates were used in transformation with four to eight transformations per plate for each expression vector. For each plate, each construct is transformed in four to eight wells. An aliquot is taken out of each transformation for the MUG assay and "nM MUG hydrolyzed" is derived from the in-plate-standard curve. An aliquot is also taken out of each transformation for the NanoLuc® reading (NanoLuc® RLU). The mean nM MUG hydrolyzed/NanoLuc® RLU for each expression vector is normalized with respect to the EXP-CaMV.35S/I-Zm.DnaK:1/T-Os.LTP:1 expression vector which is set to 100%. Table 12 shows the average of the mean for all the plates used in transformation for each expression vector comprising the synthetic 3' UTRs T-Zm.GST7.nno:2 and T-Zm.GST59.nno:1, and the controls.

TABLE 12

Average of the mean nM MUG hydrolyzed/NanoLuc ® RLU for each expression vector.

| 3' UTR | Average of Mean | Stderr |
|---|---|---|
| T-Os.LTP:1 | 100.00 | 8.09 |
| No 3' UTR | 51.95 | 4.71 |
| T-Zm.GST59.nno: 1 | 505.45 | 37.75 |
| T-Zm.GST7.nno: 2 | 345.31 | 40.73 |

As can be seen in Table 12, the expression vector without a 3' UTR provided less expression than the T-Os.LTP:1 control. Expression was enhanced by the synthetic 3' UTRs T-Zm.GST7.nno:2 and T-Zm.GST59.nno:1 compared to the T-Os.LTP:1 control. Analysis of the transcripts demonstrated proper termination imparted by the synthetic 3' UTRs T-Zm.GST7.nno:2 and T-Zm.GST59.nno:1. The synthetic 3' UTRs T-Zm.GST7.nno:2 and T-Zm.GST59.nno:1 are able to modulate expression and properly terminate transcription in transformed corn leaf protoplast cells.

Example 15

Analysis of Regulatory Elements Driving GUS in Cotton Leaf Protoplasts

Cotton leaf protoplasts were transformed with vectors, specifically expression vectors containing regulatory element groups driving expression of the β-glucuronidase (GUS) transgene. The resulting transformed cotton leaf protoplasts were analyzed for GUS protein expression to assess the effect of the selected regulatory element groups on expression.

Cotton protoplasts, derived from leaf tissue were transformed with expression vectors comprising synthetic expression elements and compared to expression elements known in the art. Separate experiments were conducted to assess the activity of the EXP's, EXP-At.GSP571 (SEQ ID NO:4), EXP-At.GSP571.nno+At.GSI21.nno:10 (SEQ ID NO:8), EXP-At.GSP571.nno+At.GSI102.nno:1 (SEQ ID NO:10), EXP-At.GSP564.nno+At.GSI17.nno:2 (SEQ ID NO:16), and EXP-At.GSP579.nno+At.GSI102.nno:3 (SEQ ID NO:22). The expression elements were cloned into expression vectors and operably linked to a GUS coding sequence, GOI-Ec.uidA+St.LS1:1:1 (SEQ ID NO:42) that comprised a processable intron. The control expression vectors comprised different configurations of known expression elements.

Two plasmids, for use in co-transformation and normalization of data, were also constructed using methods known in the art. Each plasmid contained a specific luciferase coding sequence that was driven by a constitutive EXP sequence. The plant vector pFLUC comprised a transgene cassette with a constitutive promoter operably linked 5' to an intron, (EXP-CaMV.35S-enh+Zm.DnaK:1:1, SEQ ID NO: 53), operably linked 5' to a firefly (*Photinus pyralis*) luciferase coding sequence (LUCIFERASE:1:3, SEQ ID NO: 54), operably linked 5' to a 3' UTR from the *Agrobac-* terium tumefaciens nopaline synthase gene (T-AGRtu.nos-1:1:13, SEQ ID NO: 55). The plant vector pRLUC comprised a transgene cassette with a constitutive EXP sequence (EXP-CaMV.35S-enh-Lhcb1, SEQ ID NO: 56), operably linked 5' to a sea pansy (*Renilla reniformis*) luciferase coding sequence (CR-Ren.hRenilla Lucife-0:0:1, SEQ ID NO: 57), operably linked 5' to a 3' UTR from the *Agrobacterium tumefaciens* nopaline synthase gene (T-AGRtu.nos-1:1:13, SEQ ID NO: 55).

Cotton leaf protoplasts were transformed using a PEG-based transformation method, known in the art. Protoplast cells were transformed with the plasmids, pFLUC and pRLUC, and an equimolar quantity of the EXP expression vectors. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p.02). Sample measurements were based upon multiple transformations similar to that presented in Example 14. Mean GUS/FLUC values were calculated in a similar manner as in Example 14, but were not normalized relative to the control EXP vectors.

The EXPs, EXP-At.GSP571 (SEQ ID NO:4), EXP-At.GSP571.nno+At.GSI21.nno:10 (SEQ ID NO:8), and EXP-At.GSP571.nno+At.GSI102.nno:1 (SEQ ID NO:10) were cloned into plant expression vectors operably linked 5' to a GUS coding sequence (SEQ ID NO:42), operably linked 5' to the 3' UTR, T-Mt.Sali3-2-1:2:1 (SEQ ID NO:34). Two control plant expression vectors were constructed with the EXP, EXP-At.Bglu21+At.Cyco:2 (SEQ ID NO:50), known to express poorly in cotton leaf protoplasts and the EXP, EXP-CaMV.35S-enh+Ph.DnaK:1:3 (SEQ ID NO:51), known to express well in cotton leaf protoplasts. The control EXPs were operably linked to the same GUS and 3' UTR sequence. In addition, a plant expression vector comprising a GUS transgene cassette comprising the EXP, EXP-At.GSP571 (SEQ ID NO:4), operably linked to GUS comprised the synthetic 3' UTR, T-Zm.GST7.nno:2 (SEQ ID NO:44) to assess the activity of the synthetic 3' UTR. The mean GUS/FLUC values for multiple transformations are presented in Table 13.

TABLE 13

Mean GUS/FLUC values from transformed cotton leaf protoplasts

| EXP | EXP SEQ ID NO: | 3' UTR | 3' UTR SEQ ID NO: | Mean GUS/FLUC |
|---|---|---|---|---|
| EXP-At.Bglu21 + At.Cyco: 2 | 50 | T-Mt.Sali3-2-1: 2:1 | 34 | 0.09 |
| EXP-CaMV.35S-enh + Ph.DnaK: 1:3 | 51 | T-Mt.Sali3-2-1: 2:1 | 34 | 1.70 |
| EXP-At.GSP571 | 4 | T-Mt.Sali3-2-1: 2:1 | 34 | 0.56 |
| EXP-At.GSP571.nno + At.GSI21.nno: 10 | 8 | T-Mt.Sali3-2-1: 2:1 | 34 | 1.02 |
| EXP-At.GSP571.nno + At.GSI102.nno: 1 | 10 | T-Mt.Sali3-2-1: 2:1 | 34 | 0.95 |
| EXP-At.GSP571 | 4 | T-Zm.GST7.nno: 2 | 44 | 0.46 |

As can be seen in Table 13, the EXPs, EXP-At.GSP571 (SEQ ID NO:4), EXP-At.GSP571.nno+At.GSI21.nno:2 (SEQ ID NO:8), and EXP-At.GSP571.nno+At.GSI102.nno:1 (SEQ ID NO:10) demonstrated expression in cotton leaf protoplast cells. The synthetic 3' UTR, T-Zm.GST7.nno:10 (SEQ ID NO:44) functioned in a similar manner as the endogenous 3' UTR, T-Mt.Sali3-2-1:2:1.

The EXP, EXP-At.GSP564.nno+At.GSI17.nno:2 (SEQ ID NO:16) was cloned into a plant expression vectors operably linked 5' to a GUS coding sequence (SEQ ID NO:42), operably linked 5' to the endogenous 3' UTR, T-Mt.Oxr-1:2:1 (SEQ ID NO:35). Two control plant expression vectors were constructed with the EXP, EXP-Gm.Sphas1:1:1 (SEQ ID NO:52), known to express poorly in cotton leaf protoplasts and the EXP, EXP-CaMV.35S-enh+Ph.DnaK:1:3 (SEQ ID NO:51), known to express well in cotton leaf protoplasts. The control EXPs were operably linked to the same GUS and 3' UTR sequence. The mean GUS/FLUC values for multiple transformations are presented in Table 14.

TABLE 14

Mean GUS/FLUC values from transformed cotton leaf protoplasts

| EXP | EXP SEQ ID NO: | 3' UTR | 3' UTR SEQ ID NO: | Mean GUS/FLUC |
|---|---|---|---|---|
| EXP-Gm.Sphas1: 1:1 | 52 | T-Mt.Oxr-1: 2:1 | 35 | 0.01 |
| EXP-CaMV.35S-enh + Ph.DnaK: 1:3 | 51 | T-Mt.Oxr-1: 2:1 | 35 | 2.30 |
| EXP-At.GSP564.nno + At.GSI17.nno: 2 | 16 | T-Mt.Oxr-1: 2:1 | 35 | 0.34 |

As can be seen in Table 14, the synthetic EXP, EXP-At.GSP564.nno+At.GSI17.nno:1 (SEQ ID NO:16) demonstrated expression in cotton leaf cell protoplasts.

The EXP, EXP-At.GSP579.nno+At.GSI102.nno:3 (SEQ ID NO:22) was cloned into a plant expression vectors operably linked 5' to a GUS coding sequence (SEQ ID NO:42), operably linked 5' to the endogenous 3' UTR, T-Mt.RD22-1:2:1 (SEQ ID NO:37). Two control plant expression vectors were constructed with the EXP, EXP-Gm.Sphas1:1:1 (SEQ ID NO:52), known to express poorly in cotton leaf protoplasts and the EXP, EXP-CaMV.35S-enh+Ph.DnaK:1:3 (SEQ ID NO:51), known to express well in cotton leaf protoplasts. The control EXPs were operably linked to the same GUS and 3' UTR sequence. The mean GUS/FLUC values for multiple transformations are presented in Table 15.

TABLE 15

Mean GUS/FLUC values from transformed cotton leaf protoplasts

| EXP | EXP SEQ ID NO: | 3' UTR | 3' UTR SEQ ID NO: | Mean GUS/FLUC |
|---|---|---|---|---|
| EXP-Gm.Sphas1: 1:1 | 52 | T-Mt.RD22-1: 2:1 | 37 | 0.01 |
| EXP-CaMV.35S-enh + Ph.DnaK: 1:3 | 51 | T-Mt.RD22-1: 2:1 | 37 | 2.88 |
| EXP-At.GSP579.nno + At.GSI102.nno: 3 | 22 | T-Mt.RD22-1: 2:1 | 37 | 1.19 |

As can be seen in Table 15, the synthetic EXP, EXP-At.GSP579.nno+At.GSI102.nno:3 (SEQ ID NO:22), demonstrated expression in cotton leaf cell protoplasts.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of a DNA sequence comprising the nucleotide sequence of SEQ ID NO: 27 having promoter activity and a DNA sequence comprising a fragment comprising at least 100 contiguous nucleotides of SEQ ID NO: 27, and wherein the fragment has the promoter activity of SEQ ID NO: 27.

2. The recombinant DNA molecule of claim 1, wherein the DNA sequence is operably linked to a heterologous transcribable DNA molecule.

3. The recombinant DNA molecule of claim 2, wherein the heterologous transcribable DNA molecule comprises a gene of agronomic interest.

4. The recombinant DNA molecule of claim 3, wherein the gene of agronomic interest confers herbicide tolerance in plants.

5. The recombinant DNA molecule of claim 3, wherein the gene of agronomic interest confers pest resistance in plants.

6. A transgenic plant cell comprising the recombinant DNA molecule of claim 1.

7. The transgenic plant cell of claim 6, wherein the DNA sequence is operably linked to a heterologous transcribable DNA molecule.

8. The transgenic plant cell of claim 6, wherein said transgenic plant cell is a monocotyledonous plant cell.

9. The transgenic plant cell of claim 6, wherein said transgenic plant cell is a dicotyledonous plant cell.

10. A transgenic plant, or a part thereof, wherein the transgenic plant and said part thereof comprise the recombinant DNA molecule of claim 1.

11. A progeny plant of the transgenic plant of claim 10, or a part of the progeny plant, wherein the progeny plant and said part of the progeny plant comprise the recombinant DNA molecule.

12. A transgenic seed, wherein the transgenic seed comprises the recombinant DNA molecule of claim 1.

13. A method of producing a commodity product comprising obtaining a transgenic plant or a part thereof according to claim 10 and producing the commodity product therefrom.

14. The method of claim 13, wherein the commodity product is protein concentrate, protein isolate, grain, starch, seeds, meal, flour, biomass, or seed oil.

15. A method of expressing a transcribable DNA molecule comprising obtaining a transgenic plant according to claim 10 and cultivating the transgenic plant, wherein the transcribable DNA is expressed.

\* \* \* \* \*

SEQUENCE LISTING

<160> NUMBER OF SEQ ID NOS: 57

<210> SEQ ID NO 1
<211> LENGTH: 855
<212> TYPE: DNA
<213> ORGANISM: Artificial
<220> FEATURE:
<223> OTHER INFORMATION: Synthetic EXP, EXP-At.GSP442.nno+At.Cyco:3.

<400> SEQUENCE: 1

```
tgttaatgtt atccgaacta gtcataatta caaccgacaa aataaggtta ttttgtgtgt      60
tatagaattt tttggacagt ttttgttttg gttttcgatt gtagtaaaaa tagatttatg     120
taataagatt tactttcctt gttgaaacaa aataatctta gaattaactc aacttttatg     180
ttagaacaaa tgataaaaaa atttcccctt ttctatgcga ttattttcaa tcagagagaa     240
atacatataa tatatataat tcaaattaat ctgccaaatt aataaatttg gattaaaatt     300
tataaatgaa acaatggtgt aaggcaatta aaaacacaac actaaaaata tgagaacatt     360
ttatctgggc attaagagtt tgggctttag atctaaaata aaggccggcc caacgagaat     420
attaaaccct aattgaccta gttccctata tatataaacc ctatatttct ctcgtcactc     480
ctcaactctc agctaaacca cggaccgcag gtaatttctc tcctctctat ttttaccatt     540
ttccattgac gacgatctag gttttctgat ttgattttgg agaacgcctc gatgagttta     600
tagattcgta gattggtttt gagattcagt ataatttcac ccggattcca atttttgaac     660
cgatacctaa ttttgaattg atttggtaga tcgattggtc aaatttgaaa ttgattttc      720 tccataatat ctgaagcgtc ttattggatc aaatctacaa catttctctg ttgaaaggat     780 cgatttttt tttcttggaa catgataact tttgattatt catcaaagtt ttgttctttt      840
taatatttca caggt                                                      855
```

<210> SEQ ID NO 2
<211> LENGTH: 480
<212> TYPE: DNA
<213> ORGANISM: Artificial
<220> FEATURE:
<223> OTHER INFORMATION: Synthetic promoter, P-At.GSP442.nno:2.

<400> SEQUENCE: 2

```
tgttaatgtt atccgaacta gtcataatta caaccgacaa aataaggtta ttttgtgtgt      60
tatagaattt tttggacagt ttttgttttg gttttcgatt gtagtaaaaa tagatttatg     120
taataagatt tactttcctt gttgaaacaa aataatctta gaattaactc aacttttatg     180
ttagaacaaa tgataaaaaa atttcccctt ttctatgcga ttattttcaa tcagagagaa     240
```

```
atacatataa tatatataat tcaaattaat ctgccaaatt aataaatttg gattaaaatt    300
tataaatgaa acaatggtgt aaggcaatta aaaacacaac actaaaaata tgagaacatt    360
ttatctgggc attaagagtt tgggctttag atctaaaata aaggccggcc caacgagaat    420
attaaaccct aattgaccta gttccctata tatataaacc ctatatttct ctcgtcactc    480
```

<210> SEQ ID NO 3
<211> LENGTH: 20
<212> TYPE: DNA
<213> ORGANISM: Artificial
<220> FEATURE:
<223> OTHER INFORMATION: Synthetic leader, L-At.GSP442.nno:1.

<400> SEQUENCE: 3

```
ctcaactctc agctaaacca                                                 20
```

<210> SEQ ID NO 4
<211> LENGTH: 500
<212> TYPE: DNA
<213> ORGANISM: Artificial
<220> FEATURE:
<223> OTHER INFORMATION: Synthetic EXP, EXP-At.GSP571.

<400> SEQUENCE: 4

```
agtacaatca tacaagagca atatatatat ttttggttat tgaaatttaa atatcatctt     60
cacaaaatga aaaagcacaa aaagtattaa ttaatatcat gttttgagac tcctttttac    120
caagaatata aatttcacac ctaagaaaat tctgaactag gaaataacc agcatacaat    180 taaggaataa gaaaatgcaa ttacgataaa cacttgtcac aaattgttta ataagtcact    240
atccaatcaa ttatcaaaag taagatattg ccacgtggca accagtattt tcatcacctt    300
atcaaaagat aagcaaaaga accacatcaa agccacaaaa tgccaaccac agatggataa    360
ggaaaatcca accaaccaca tgtaatccca cacctcatca ccttatccac acctctgtct    420
atatatataa acacacactt cgtaaccact catcactcac cacaaacaga gaatatctca    480
tctcttctta gcaaacaaag                                                500
```

<210> SEQ ID NO 5
<211> LENGTH: 500
<212> TYPE: DNA
<213> ORGANISM: Artificial
<220> FEATURE:
<223> OTHER INFORMATION: Synthetic promoter, P-At.GSP571.nno:5.

<400> SEQUENCE: 5

```
agtacaatca tacaagagca atatatatat ttttggttat tgaaatttaa atatcatctt     60
cacaaaatga aaaagcacaa aaagtattaa ttaatatcat gttttgagac tcctttttac    120
caagaatata aatttcacac ctaagaaaat tctgaactag gaaataacc agcatacaat    180 taaggaataa gaaaatgcaa ttacgataaa cacttgtcac aaattgttta ataagtcact    240
atccaatcaa ttatcaaaag taagatattg ccacgtggca accagtattt tcatcacctt    300
atcaaaagat aagcaaaaga accacatcaa agccacaaaa tgccaaccac agatggataa    360
ggaaaatcca accaaccaca tgtaatccca cacctcatca ccttatccac acctctgtct    420
atatatataa acacacactt cgtaaccact catcactcac cacaaacaga gaatatctca    480
tctcttctta gcaaacaaag                                                500
```

<210> SEQ ID NO 6

```
<211> LENGTH: 49
<212> TYPE: DNA
<213> ORGANISM: Artificial
<220> FEATURE:
<223> OTHER INFORMATION: Synthetic leader, L-At.GSP571.nno:1.

<400> SEQUENCE: 6
atcactcacc acaaacagag aatatctcat ctcttcttag caaacaaag          49

<210> SEQ ID NO 7
<211> LENGTH: 855
<212> TYPE: DNA
<213> ORGANISM: Artificial
<220> FEATURE:
<223> OTHER INFORMATION: Synthetic EXP, EXP-At.GSP571.nno+At.Cyco:2.

<400> SEQUENCE: 7
agtacaatca tacaagagca atatatatat ttttggttat tgaaatttaa atatcatctt    60
cacaaaatga aaaagcacaa aaagtattaa ttaatatcat gttttgagac tccttttac   120 caagaatata aatttcacac ctaagaaaat tctgaactag gaaataaacc agcatacaat   180
taaggaataa gaaaatgcaa ttacgataaa cacttgtcac aaattgttta ataagtcact   240
atccaatcaa ttatcaaaag taagatattg ccacgtggca accagtattt tcatcacctt   300
atcaaaagat aagcaaaaga accacatcaa agccacaaaa tgccaaccac agatggataa   360
ggaaaatcca accaaccaca tgtaatccca cacctcatca ccttatccac acctctgtct   420
atatatataa acacacactt cgtaaccact catcactcac cacaaacaga gaatatctca   480
tctcttctta gcaaacaaag cggaccgcag gtaatttctc tcctctctat ttttaccatt   540
ttccattgac gacgatctag gttttctgat tgattttgg agaacgcctc gatgagttta   600
tagattcgta gattggtttt gagattcagt ataatttcac ccggattcca atttttgaac   660
cgatacctaa ttttgaattg atttggtaga tcgattggtc aaatttgaaa ttgattttc    720 tccataatat ctgaagcgtc ttattggatc aaatctacaa catttctctg ttgaaaggat   780
cgattttttt tttcttggaa catgataact tttgattatt catcaaagtt ttgttctttt    840
taatatttca caggt                                                  855

<210> SEQ ID NO 8
<211> LENGTH: 816
<212> TYPE: DNA
<213> ORGANISM: Artificial
<220> FEATURE:
<223> OTHER INFORMATION: Synthetic EXP, EXP-At.GSP571.nno+At.GSI21.nno:
      10.

<400> SEQUENCE: 8
agtacaatca tacaagagca atatatatat ttttggttat tgaaatttaa atatcatctt    60
cacaaaatga aaaagcacaa aaagtattaa ttaatatcat gttttgagac tccttttac   120 caagaatata aatttcacac ctaagaaaat tctgaactag gaaataaacc agcatacaat   180
taaggaataa gaaaatgcaa ttacgataaa cacttgtcac aaattgttta ataagtcact   240
atccaatcaa ttatcaaaag taagatattg ccacgtggca accagtattt tcatcacctt   300
atcaaaagat aagcaaaaga accacatcaa agccacaaaa tgccaaccac agatggataa   360
ggaaaatcca accaaccaca tgtaatccca cacctcatca ccttatccac acctctgtct   420
atatatataa acacacactt cgtaaccact catcactcac cacaaacaga gaatatctca   480
tctcttctta gcaaacaaag cggaccgcag gtttattctt ctctctctat cctctctctt   540
```

-continued

```
ctgatctcga tttgttttttt tcgaatcgct ctacttccag ttagattctt gatttgagat    600
taattagatt gattattcta atcgtttttt ttgtaagcaa ttaagattta tcttgtttta    660 tgttttctt taggtatgac ttgttatgta tgtcactgtt tcagatctga tcctctctgt    720
tggtttgtga attctcttgt attgttctaa tcactgtttc tgaatttgat tcgggttttt    780
attgaattct ttttatgtgt tttggtattt gcaggt                              816
```

<210> SEQ ID NO 9
<211> LENGTH: 309
<212> TYPE: DNA
<213> ORGANISM: Artificial
<220> FEATURE:
<223> OTHER INFORMATION: Synthetic intron, I-At.GSI21.nno:2.

<400> SEQUENCE: 9

```
caggtttatt cttctctctc tatcctctct cttctgatct cgatttgttt ttttcgaatc     60
gctctacttc cagttagatt cttgatttga gattaattag attgattatt ctaatcgttt    120
tttttgtaag caattaagat ttatcttgtt ttatgttttt ctttaggtat gacttgttat    180
gtatgtcact gtttcagatc tgatcctctc tgttggtttg tgaattctct tgtattgttc    240
taatcactgt ttctgaattt gattcgggtt tttattgaat tcttttatg tgttttggta    300 tttgcaggt                                                            309
```

<210> SEQ ID NO 10
<211> LENGTH: 810
<212> TYPE: DNA
<213> ORGANISM: Artificial
<220> FEATURE:
<223> OTHER INFORMATION: Synthetic EXP, EXP-At.GSP571.nno+At.GSI102.nno:
      1.

<400> SEQUENCE: 10

```
agtacaatca tacaagagca atatatatat ttttggttat tgaaatttaa atatcatctt     60
cacaaaatga aaagcacaa aaagtattaa ttaatatcat gttttgagac tccttttttac    120 caagaatata aatttcacac ctaagaaaat tctgaactag gaaaataacc agcatacaat    180
taaggaataa gaaaatgcaa ttacgataaa cacttgtcac aaattgttta ataagtcact    240
atccaatcaa ttatcaaaag taagatattg ccacgtggca accagtattt tcatcacctt    300
atcaaaagat aagcaaaaga accacatcaa agccacaaaa tgccaaccac agatggataa    360
ggaaaatcca accaaccaca tgtaatccca cacctcatca ccttatccac acctctgtct    420
atatatataa acacacactt cgtaaccact catcactcac cacaaacaga gaatatctca    480
tctcttctta gcaaacaaag tttcaggttt agctttctct ccgatctcgg ctttcgatct    540
gatctcgtct gatctccgat ttcgatcccc gtccgatctc gatctgatcc catccgatct    600
gtgattgatt cgttgagatt cagatctgat cttaggatct ctctgataga tcatagattc    660
aatctctcga gatagagatg attgatgttg ttcagatcgg ttttgatctc tgatctgatc    720
agctcgattg attcgatttg attctcgatt cgatttgatc gacaattgat ctgattctct    780
aattgatgtt ctgttttttgt tacaggtttt                                    810
```

<210> SEQ ID NO 11
<211> LENGTH: 310
<212> TYPE: DNA
<213> ORGANISM: Artificial
<220> FEATURE:
<223> OTHER INFORMATION: Synthetic intron, I-At.GSI102.nno:1.

<400> SEQUENCE: 11

```
tttcaggttt agctttctct ccgatctcgg ctttcgatct gatctcgtct gatctccgat    60
ttcgatcccc gtccgatctc gatctgatcc catccgatct gtgattgatt cgttgagatt   120
cagatctgat cttaggatct ctctgataga tcatagattc aatctctcga gatagagatg   180
attgatgttg ttcagatcgg ttttgatctc tgatctgatc agctcgattg attcgatttg   240
attctcgatt cgatttgatc gacaattgat ctgattctct aattgatgtt ctgttttgt    300
tacaggtttt                                                           310
```

<210> SEQ ID NO 12
<211> LENGTH: 500
<212> TYPE: DNA
<213> ORGANISM: Artificial
<220> FEATURE:
<223> OTHER INFORMATION: Synthetic EXP, EXP-At.GSP564.

<400> SEQUENCE: 12

```
agagttacaa tatagagaaa aaatgtattc tgtgtttttc acttttcttc ttctttgaaa    60
atccaaaaac aactatttat tgattggcaa attgcatcaa attttcatg ctaaatccaa    120
cataaatata aaatctttta atcaaataca gaatctaaag atagtagggt ttttttttatt  180
taaaatgatg tttcaaaaaa ttagaaagca tgttttccac acttggaaaa tataaataaa   240
ttaagattta ttttttccca aacaagataa atctataaat attcatcaca atcacgtgta   300
caaaaataaa tccaacaaga gataaggata agccaacgga cccatatatt aggcccattt   360
taaaataagg aaataagcag ataattatcc accaccttat ccaaaaccct agatccacaa   420
cataaatctc tataaaaacc cttttcactc acactcacat cactcacata agaactaaaa   480
tctctaaaga gtcgtctctg                                                500
```

<210> SEQ ID NO 13
<211> LENGTH: 461
<212> TYPE: DNA
<213> ORGANISM: Artificial
<220> FEATURE:
<223> OTHER INFORMATION: Synthetic promoter, P-At.GSP564.nno:3.

<400> SEQUENCE: 13

```
agagttacaa tatagagaaa aaatgtattc tgtgtttttc acttttcttc ttctttgaaa    60
atccaaaaac aactatttat tgattggcaa attgcatcaa attttcatg ctaaatccaa    120
cataaatata aaatctttta atcaaataca gaatctaaag atagtagggt ttttttttatt  180
taaaatgatg tttcaaaaaa ttagaaagca tgttttccac acttggaaaa tataaataaa   240
ttaagattta ttttttccca aacaagataa atctataaat attcatcaca atcacgtgta   300
caaaaataaa tccaacaaga gataaggata agccaacgga cccatatatt aggcccattt   360
taaaataagg aaataagcag ataattatcc accaccttat ccaaaaccct agatccacaa   420
cataaatctc tataaaaacc cttttcactc acactcacat c                       461
```

<210> SEQ ID NO 14
<211> LENGTH: 39
<212> TYPE: DNA
<213> ORGANISM: Artificial
<220> FEATURE:
<223> OTHER INFORMATION: Synthetic leader, L-At.GSP564.nno:1.

<400> SEQUENCE: 14

```
actcacataa gaactaaaat ctctaaagag tcgtctctg                           39
```

<210> SEQ ID NO 15
<211> LENGTH: 855
<212> TYPE: DNA
<213> ORGANISM: Artificial
<220> FEATURE:
<223> OTHER INFORMATION: Synthetic EXP, EXP-At.GSP564.nno+At.Cyco:2.

<400> SEQUENCE: 15

```
agagttacaa tatagagaaa aaatgtattc tgtgtttttc acttttcttc ttctttgaaa    60
atccaaaaac aactatttat tgattggcaa attgcatcaa attttcatg ctaaatccaa    120
cataaatata aaatctttta atcaaataca gaatctaaag atagtagggt ttttttatt    180
taaaatgatg tttcaaaaaa ttagaaagca tgttttccac acttggaaaa tataaataaa   240
ttaagattta ttttttccca aacaagataa atctataaat attcatcaca atcacgtgta   300
caaaaataaa tccaacaaga gataaggata agccaacgga cccatatatt aggcccattt    360
taaaataagg aaataagcag ataattatcc accaccttat ccaaaccct agatccacaa    420
cataaatctc tataaaaacc cttttcactc acactcacat cactcacata agaactaaaa   480
tctctaaaga gtcgtctctg cggaccgcag gtaatttctc tcctctctat ttttaccatt   540
ttccattgac gacgatctag gttttctgat ttgattttgg agaacgcctc gatgagttta   600
tagattcgta gattggtttt gagattcagt ataatttcac ccggattcca attttttgaac  660
cgatacctaa ttttgaattg atttggtaga tcgattggtc aaatttgaaa ttgatttttc   720
tccataatat ctgaagcgtc ttattggatc aaatctacaa catttctctg ttgaaaggat   780
cgattttttt tttcttggaa catgataact tttgattatt catcaaagtt ttgttctttt   840
taatatttca caggt                                                   855
```

<210> SEQ ID NO 16
<211> LENGTH: 807
<212> TYPE: DNA
<213> ORGANISM: Artificial
<220> FEATURE:
<223> OTHER INFORMATION: Synthetic EXP, EXP-At.GSP564.nno+At.GSI17.nno:
      2.

<400> SEQUENCE: 16

```
agagttacaa tatagagaaa aaatgtattc tgtgtttttc acttttcttc ttctttgaaa    60
atccaaaaac aactatttat tgattggcaa attgcatcaa attttcatg ctaaatccaa    120
cataaatata aaatctttta atcaaataca gaatctaaag atagtagggt ttttttatt    180
taaaatgatg tttcaaaaaa ttagaaagca tgttttccac acttggaaaa tataaataaa   240
ttaagattta ttttttccca aacaagataa atctataaat attcatcaca atcacgtgta   300
caaaaataaa tccaacaaga gataaggata agccaacgga cccatatatt aggcccattt    360
taaaataagg aaataagcag ataattatcc accaccttat ccaaaccct agatccacaa    420
cataaatctc tataaaaacc cttttcactc acactcacat cactcacata agaactaaaa   480
tctctaaaga gtcgtctctg cggaccgcag gtaaacccag atctctttct tctcttctct   540
tcatctcgat ctctccattt tcataaaccc aattttttct ctgatttgtt tgatttggtt   600
tggatctttc tgtgtttcca tggttttagg aattttagga tagattttg tttgttcatg   660
ttattcatcg gatatataga tttcaaattc ttttgcaatt tttctctctc tttagttttg   720
ctcaattttg gttgttgttg tgatgagtgt tctcttatg ggtttatctg agcttggtga    780
gagttttttg atattgattt tgcaggt                                      807
```

<210> SEQ ID NO 17
<211> LENGTH: 300
<212> TYPE: DNA
<213> ORGANISM: Artificial
<220> FEATURE:
<223> OTHER INFORMATION: Synthetic intron, I-At.GSI17.nno:1.

<400> SEQUENCE: 17

```
caggtaaacc cagatctctt tcttctcttc tcttcatctc gatctctcca tttcataaa        60
cccaattttt tctctgattt gtttgatttg gtttggatct ttctgtgttt ccatggtttt      120
aggaattta ggatagattt tgtttgttc atgttattca tcggatatat agatttcaaa       180
ttctttttgca attttctct ctctttagtt ttgctcaatt ttggttgttg ttgtgatgag      240
tgttctcttt atgggtttat ctgagcttgg tgagagtttt tgatattga ttttgcaggt      300
```

<210> SEQ ID NO 18
<211> LENGTH: 810
<212> TYPE: DNA
<213> ORGANISM: Artificial
<220> FEATURE:
<223> OTHER INFORMATION: Synthetic EXP, EXP-At.GSP564.nno+At.GSI102.nno:
    1.

<400> SEQUENCE: 18

```
agagttacaa tatagagaaa aaatgtattc tgtgttttc acttttcttc ttctttgaaa        60
atccaaaaac aactatttat tgattggcaa attgcatcaa attttcatg ctaaatccaa       120
cataaatata aaatctttta atcaaataca gaatctaaag atagtagggt ttttttat       180
taaaatgatg tttcaaaaaa ttagaaagca tgttttccac acttggaaaa tataaataaa     240
ttaagattta tttttccca aacaagataa atctataaat attcatcaca atcacgtgta     300
caaaaataaa tccaacaaga gataaggata agccaacgga cccatatatt aggcccattt     360
taaaataagg aaataagcag ataattatcc accaccttat ccaaaaccct agatccacaa     420
cataaatctc tataaaaacc cttttcactc acactcacat cactcacata agaactaaaa     480
tctctaaaga gtcgtctctg tttcaggttt agctttctct ccgatctcgg ctttcgatct     540
gatctcgtct gatctccgat ttcgatcccc gtccgatctc gatctgatcc catccgatct     600
gtgattgatt cgttgagatt cagatctgat cttaggatct ctctgataga tcatagattc     660
aatctctcga gatagagatg attgatgttg ttcagatcgg ttttgatctc tgatctgatc     720
agctcgattg attcgatttg attctcgatt cgatttgatc gacaattgat ctgattctct     780
aattgatgtt ctgttttgt tacaggtttt                                        810
```

<210> SEQ ID NO 19
<211> LENGTH: 500
<212> TYPE: DNA
<213> ORGANISM: Artificial
<220> FEATURE:
<223> OTHER INFORMATION: Synthetic EXP, EXP-At.GSP579.

<400> SEQUENCE: 19

```
catagagcag tcttgtctca aaaaaatcga attaagcagt tgaaagtgtt cgtcttatca        60
agatgaaaat ctgacaaaaa ttttgttaaa atttggtagt atttgataag atatgtacct      120
taaaattgat gttaataatc ttcttatcca aaaaaagaac caatccattg cagtcttaaa      180
tgaaatattt caagaaagga ttgagccaaa aaccgtgttt ataaaattt caaatccaca      240
atttccacat tcacttggat attacaagtg tggcatctca taaaaaaaaa gaaaaagaaa      300
```

```
aaccacgtgg actattatat ccagccacgt ggctttaaaa tcttatccaa aatcacctct    360
catccaacgg ataaggtaac cacacagcct tatccaacca catcacacga atccactcta    420
tatatactcc atataaccat cactcacacg tctttcatca cacaagtaaa acagcatcac    480
taaaagaaaa aaaacaagaa                                                500

<210> SEQ ID NO 20
<211> LENGTH: 449
<212> TYPE: DNA
<213> ORGANISM: Artificial
<220> FEATURE:
<223> OTHER INFORMATION: Synthetic promoter, P-At.GSP579.nno:2.

<400> SEQUENCE: 20
catagagcag tcttgtctca aaaaaatcga attaagcagt tgaaagtgtt cgtcttatca     60
agatgaaaat ctgacaaaaa ttttgttaaa atttggtagt atttgataag atatgtacct    120
taaaattgat gttaataatc ttcttatcca aaaaaagaac caatccattg cagtcttaaa    180
tgaaatattt caagaaagga ttgagccaaa accgtgtttt ataaaatttt caaatccaca    240
atttccacat tcacttggat attacaagtg tggcatctca taaaaaaaaa gaaaagaaa     300 aaccacgtgg actattatat ccagccacgt ggctttaaaa tcttatccaa aatcacctct    360
catccaacgg ataaggtaac cacacagcct tatccaacca catcacacga atccactcta    420
tatatactcc atataaccat cactcacac                                      449

<210> SEQ ID NO 21
<211> LENGTH: 51
<212> TYPE: DNA
<213> ORGANISM: Artificial
<220> FEATURE:
<223> OTHER INFORMATION: Synthetic leader, L-At.GSP579.nno:1.

<400> SEQUENCE: 21
gtctttcatc acacaagtaa aacagcatca ctaaaagaaa aaaacaaga a               51

<210> SEQ ID NO 22
<211> LENGTH: 810
<212> TYPE: DNA
<213> ORGANISM: Artificial
<220> FEATURE:
<223> OTHER INFORMATION: Synthetic EXP, EXP-At.GSP579.nno+At.GSI102.nno:
    3.

<400> SEQUENCE: 22
catagagcag tcttgtctca aaaaaatcga attaagcagt tgaaagtgtt cgtcttatca     60
agatgaaaat ctgacaaaaa ttttgttaaa atttggtagt atttgataag atatgtacct    120
taaaattgat gttaataatc ttcttatcca aaaaaagaac caatccattg cagtcttaaa    180
tgaaatattt caagaaagga ttgagccaaa accgtgtttt ataaaatttt caaatccaca    240
atttccacat tcacttggat attacaagtg tggcatctca taaaaaaaaa gaaaagaaa     300 aaccacgtgg actattatat ccagccacgt ggctttaaaa tcttatccaa aatcacctct    360
catccaacgg ataaggtaac cacacagcct tatccaacca catcacacga atccactcta    420
tatatactcc atataaccat cactcacacg tctttcatca cacaagtaaa acagcatcac    480
taaaagaaaa aaaacaagaa tttcaggttt agctttctct ccgatctcgg ctttcgatct    540
gatctcgtct gatctccgat ttcgatcccc gtccgatctc gatctgatcc catccgatct    600
gtgattgatt cgttgagatt cagatctgat cttaggatct ctctgataga tcatagattc    660
```

| | |
|---|---|
| aatctctcga gatagagatg attgatgttg ttcagatcgg ttttgatctc tgatctgatc | 720 |
| agctcgattg attcgatttg attctcgatt cgatttgatc gacaattgat ctgattctct | 780 |
| aattgatgtt ctgttttgt tacaggtttt | 810 |

<210> SEQ ID NO 23
<211> LENGTH: 1350
<212> TYPE: DNA
<213> ORGANISM: Artificial
<220> FEATURE:
<223> OTHER INFORMATION: Synthetic EXP, EXP-At.GSP571.nno+At.GSP442.
    nno+At.Cyco:1.

<400> SEQUENCE: 23

| | |
|---|---|
| agtacaatca tacaagagca atatatatat ttttggttat tgaaatttaa atatcatctt | 60 |
| cacaaaatga aaaagcacaa aaagtattaa ttaatatcat gttttgagac tcctttttac | 120 |
| caagaatata aatttcacac ctaagaaaat tctgaactag gaaaataacc agcatacaat | 180 |
| taaggaataa gaaaatgcaa ttcgataaa cacttgtcac aaattgttta ataagtcact | 240 |
| atccaatcaa ttatcaaaag taagatattg ccacgtggca accagtattt tcatcacctt | 300 |
| atcaaaagat aagcaaaaga accacatcaa agccacaaaa tgccaaccac agatggataa | 360 |
| ggaaaatcca accaaccaca tgtaatccca cacctcatca ccttatccac acctctgtct | 420 |
| attgttaatg ttatccgaac tagtcataat tacaaccgac aaaataaggt tattttgtgt | 480 |
| gttatagaat ttttggaca gtttttgttt tggttttcga ttgtagtaaa aatagattta | 540 |
| tgtaataaga tttacttttc ttgttgaaac aaaataatct tagaattaac tcaacttta | 600 |
| tgttagaaca aatgataaaa aaatttcccc ttttctatgc gattattttc aatcagagag | 660 |
| aaatacatat aatatatata attcaaatta atctgccaaa ttaataaatt tggattaaaa | 720 |
| tttataaatg aaacaatggt gtaaggcaat taaaaacaca acactaaaaa tatgagaaca | 780 |
| ttttatctgg gcattaagag tttgggcttt agatctaaaa taaaggccgg cccaacgaga | 840 |
| atattaaacc ctaattgacc tagttcccta tatatataaa ccctatattt ctctcgtcac | 900 |
| tcctcaactc tcagctaaac cacggaccgc agtgagtcac ataaccctct ggaaagagt | 960 |
| ctcaacactt gcagagaaaa agaacaagga agatcccgga acaggtaat ttctctcctc | 1020 |
| tctatttta ccattttcca ttgacgacga tctaggtttt ctgatttgat tttggagaac | 1080 |
| gcctcgatga gtttatagat tcgtagattg gttttgagat tcagtataat ttcaccccgga | 1140 |
| ttccaatttt tgaaccgata cctaatttttg aattgatttg gtagatcgat tggtcaaatt | 1200 |
| tgaaattgat ttttctccat aatatctgaa gcgtcttatt ggatcaaatc tacaacatt | 1260 |
| ctctgttgaa aggatcgatt ttttttttct tggaacatga taactttga ttattcatca | 1320 |
| aagttttgtt cttttaata tttcacaggt | 1350 |

<210> SEQ ID NO 24
<211> LENGTH: 422
<212> TYPE: DNA
<213> ORGANISM: Artificial
<220> FEATURE:
<223> OTHER INFORMATION: Synthetic enhancer, E-At.GSP571.nno:1.

<400> SEQUENCE: 24

| | |
|---|---|
| agtacaatca tacaagagca atatatatat ttttggttat tgaaatttaa atatcatctt | 60 |
| cacaaaatga aaaagcacaa aaagtattaa ttaatatcat gttttgagac tcctttttac | 120 |
| caagaatata aatttcacac ctaagaaaat tctgaactag gaaaataacc agcatacaat | 180 |

```
taaggaataa gaaaatgcaa ttacgataaa cacttgtcac aaattgttta ataagtcact    240
atccaatcaa ttatcaaaag taagatattg ccacgtggca accagtattt tcatcacctt    300
atcaaaagat aagcaaaaga accacatcaa agccacaaaa tgccaaccac agatggataa    360
ggaaaatcca accaaccaca tgtaatccca cacctcatca ccttatccac acctctgtct    420
at                                                                  422
```

<210> SEQ ID NO 25
<211> LENGTH: 902
<212> TYPE: DNA
<213> ORGANISM: Artificial
<220> FEATURE:
<223> OTHER INFORMATION: Synthetic chimeric promoter, P-At.GSP571/442.

<400> SEQUENCE: 25

```
agtacaatca tacaagagca atatatatat ttttggttat tgaaatttaa atatcatctt     60
cacaaaatga aaaagcacaa aaagtattaa ttaatatcat gttttgagac tccttttac    120 caagaatata aatttcacac ctaagaaaat tctgaactag gaaaataacc agcatacaat    180
taaggaataa gaaaatgcaa ttacgataaa cacttgtcac aaattgttta ataagtcact    240
atccaatcaa ttatcaaaag taagatattg ccacgtggca accagtattt tcatcacctt    300
atcaaaagat aagcaaaaga accacatcaa agccacaaaa tgccaaccac agatggataa    360
ggaaaatcca accaaccaca tgtaatccca cacctcatca ccttatccac acctctgtct    420
attgttaatg ttatccgaac tagtcataat tacaaccgac aaaataaggt tattttgtgt    480
gttatagaat ttttggaca gttttgtttt tggttttcga ttgtagtaaa aatagattta    540
tgtaataaga tttactttc ttgttgaaac aaaataatct tagaattaac tcaacttta    600 tgttagaaca aatgataaaa aaatttcccc ttttctatgc gattattttc aatcagagag    660
aaatacatat aatatatata attcaaatta atctgccaaa ttaataaatt tggattaaaa    720
tttataaatg aaacaatggt gtaaggcaat taaaaacaca acactaaaaa tatgagaaca    780
ttttatctgg gcattaagag tttgggcttt agatctaaaa taaaggccgg cccaacgaga    840
atattaaacc ctaattgacc tagttcccta tatatataaa ccctataTTT ctctcgtcac    900
tc                                                                  902
```

<210> SEQ ID NO 26
<211> LENGTH: 800
<212> TYPE: DNA
<213> ORGANISM: Artificial
<220> FEATURE:
<223> OTHER INFORMATION: Synthetic EXP, EXP-At.GSP576.nno+At.GSI17.nno:
     3.

<400> SEQUENCE: 26

```
aattaaattc aacacgtttg ttatatattt tttattgaaa ttattcttca ttcgtctttt     60
aatggataaa aagtataat caagtatatt ttatacacat ctttctattt gtgtgtacca    120
aatgttaaaa tggccaattt tgaccaaaaa accgcataat tttcttaatt tcttaaatat    180
gattaattca tcaataactt ggaatttcac aatacacaaa agtgggtgta gttaccgtta    240
ttatatttat acacaacaac tcatctcctc atagaaagaa aagaaaaata aataagaaa    300 tcaaaaaacg acaagataac caatctccac atcatccacg tggcgtaagg ataaggtcac    360
aaccaccact cagccacgtg gcagaatctt atccaatcac tctcaccaca caaacccttat    420 ccacttctat atataatctc ttcttctcat tatcactcac cacacatcct tgcaaaagta    480
```

```
aagagaaaaa acaaacaaga caggtaaacc cagatctctt tcttctcttc tcttcatctc    540
gatctctcca ttttcataaa cccaatttt tctctgattt gtttgatttg gtttggatct    600
ttctgtgttt ccatggtttt aggaatttta ggatagattt ttgtttgttc atgttattca    660
tcggatatat agatttcaaa ttcttttgca attttctct ctctttagtt ttgctcaatt    720
ttggttgttg tgtgatgag tgttctcttt atgggtttat ctgagcttgg tgagagtttt    780
ttgatattga ttttgcaggt                                                 800
```

<210> SEQ ID NO 27
<211> LENGTH: 458
<212> TYPE: DNA
<213> ORGANISM: Artificial
<220> FEATURE:
<223> OTHER INFORMATION: Synthetic promoter, P-At.GSP576.nno:4.

<400> SEQUENCE: 27

```
aattaaattc aacacgtttg ttatatattt tttattgaaa ttattcttca ttcgtctttt     60
aatggataaa aaggtataat caagtatatt ttatacacat cttctatttt gtgtgtacca    120
aatgttaaaa tggccaattt tgaccaaaaa accgcataat tttcttaatt tcttaaatat    180
gattaattca tcaataactt ggaatttcac aatacacaaa agtgggtgta gttaccgtta    240
ttatatttat acacaacaac tcatctcctc atagaaagaa aagaaaaata aataagaaa     300 tcaaaaaacg acaagataac caatctccac atcatccacg tggcgtaagg ataaggtcac    360
aaccaccact cagccacgtg gcagaatctt atccaatcac tctcaccaca caaaccttat    420
ccacttctat atataatctc ttcttctcat tatcactc                             458
```

<210> SEQ ID NO 28
<211> LENGTH: 42
<212> TYPE: DNA
<213> ORGANISM: Artificial
<220> FEATURE:
<223> OTHER INFORMATION: Synthetic leader, L-At.GSP576.nno:2.

<400> SEQUENCE: 28

```
accacacatc cttgcaaaag taaagagaaa aaacaaacaa ga                         42
```

<210> SEQ ID NO 29
<211> LENGTH: 400
<212> TYPE: DNA
<213> ORGANISM: Artificial
<220> FEATURE:
<223> OTHER INFORMATION: Synthetic 3' UTR, T-Zm.GST59.nno:1.

<400> SEQUENCE: 29

```
ttgttttgtt tgtaccataa tatatttgct gtgtgtttgc tgccatctca tgtgcagagg     60
aatatatatt ttttcgtggt ttctgtcgtg ctgtactgag gaccgttgta acatatgaa     120 taaaagtaat aaatttgttt tttgtttcat accccattgg tggtgctcct ttggttctcg    180
tttgttgctg gagacagata tgtttgtgtt gtttgtgttc ttgttttatc tggaggcgag    240 cagcttttg tttgggaaga acaaaatcag tttggatgct ttgctccatc ctgtactgtt    300
gtaaactgca tatatatata tatatgaa taaaactggt tttgtttcat accatgtttg    360
tgtgttctgt tctgttgctc gagacgagga ataaattgtt                          400
```

<210> SEQ ID NO 30
<211> LENGTH: 947
<212> TYPE: DNA

<213> ORGANISM: Artificial
<220> FEATURE:
<223> OTHER INFORMATION: Synthetic EXP, EXP-At.GSP221+At.Cyco:3.

<400> SEQUENCE: 30

```
gctagcgctt atggagcgtg atggactgaa agagacccct accacgtgtt gacgtaagca    60
atgacataaa accgatccta atctctccta cgaacgacag cggagagtac tgctgaaagc   120
tatgctttta tttttcttta tttttctcgt cagtggaata cacgttttgt cggtgtgtgt   180
cctttttccaa agaaagacgg aactgcctag acaacgtcg gctaccaaag cacaatgtaa   240
agtagacatg atgatcgacg acgtcatgca tgacgtttaa catgcattgt atgtgtccgt   300
cagtctataa ataggtcaag aacaaacatc gagaaaaggc agaggcgaaa tacccatctg   360
cctatctctc aagaaataac tctctcttgt tcttcatcct ttctttcata gtttaaaaac   420
ctgaaattgg gcaagcccca taggcatttt ggtatcagag cgagtaagga caagtaggta   480
agtccctaaa atacttctat caataaaatt tctacgccaa gaagggtaag ttgtacgttt   540
atcctacacc cttgtgtttg taaccaggct tggtcaagtg cacaagggta tttgagtccc   600
aggtaatttc tctcctctct atttttacca ttttccattg acgacgatct aggttttctg   660
atttgatttt ggagaacgcc tcgatgagtt tatagattcg tagattggtt ttgagattca   720
gtataatttc acccggattc caattttttga accgatacct aattttgaat tgatttggta   780
gatcgattgg tcaaatttga aattgatttt tctccataat atctgaagcg tcttattgga   840
tcaaatctac aacatttctc tgttgaaagg atcgattttt ttttttcttgg aacatgataa   900
cttttgatta ttcatcaaag ttttgttctt tttaatattt cacaggt            947
```

<210> SEQ ID NO 31
<211> LENGTH: 370
<212> TYPE: DNA
<213> ORGANISM: Artificial
<220> FEATURE:
<223> OTHER INFORMATION: Synthetic promoter, P-At.GSP221:3.

<400> SEQUENCE: 31

```
gctagcgctt atggagcgtg atggactgaa agagacccct accacgtgtt gacgtaagca    60
atgacataaa accgatccta atctctccta cgaacgacag cggagagtac tgctgaaagc   120
tatgctttta tttttcttta tttttctcgt cagtggaata cacgttttgt cggtgtgtgt   180
cctttttccaa agaaagacgg aactgcctag acaacgtcg gctaccaaag cacaatgtaa   240
agtagacatg atgatcgacg acgtcatgca tgacgtttaa catgcattgt atgtgtccgt   300
cagtctataa ataggtcaag aacaaacatc gagaaaaggc agaggcgaaa tacccatctg   360
cctatctctc                                                          370
```

<210> SEQ ID NO 32
<211> LENGTH: 229
<212> TYPE: DNA
<213> ORGANISM: Artificial
<220> FEATURE:
<223> OTHER INFORMATION: Synthetic leader, L-At.GSP221:1.

<400> SEQUENCE: 32

```
aagaaataac tctctcttgt tcttcatcct ttctttcata gtttaaaaac ctgaaattgg    60
gcaagcccca taggcatttt ggtatcagag cgagtaagga caagtaggta agtccctaaa   120
atacttctat caataaaatt tctacgccaa gaagggtaag ttgtacgttt atcctacacc   180
cttgtgtttg taaccaggct tggtcaagtg cacaagggta tttgagtcc               229
```

<210> SEQ ID NO 33
<211> LENGTH: 348
<212> TYPE: DNA
<213> ORGANISM: Arabidopsis thaliana
<220> FEATURE:
<221> NAME/KEY: misc_feature
<222> LOCATION: (1)..(348)
<223> OTHER INFORMATION: An intron, I-At.Cyco:2 derived from a
      Cytochrome c oxidase subunit VIa gene from Arabidopsis.

<400> SEQUENCE: 33
caggtaattt ctctcctctc tattttacc atttcccatt gacgacgatc taggttttct      60
gatttgattt tggagaacgc ctcgatgagt ttatagattc gtagattggt tttgagattc    120
agtataattt cacccggatt ccaattttg aaccgatacc taattttgaa ttgatttggt    180
agatcgattg gtcaaatttg aaattgattt ttctccataa tatctgaagc gtcttattgg    240
atcaaatcta caacatttct ctgttgaaag gatcgatttt tttttcttg gaacatgata    300 actttgatt attcatcaaa gtttgttct tttaatatt tcacaggt                   348

<210> SEQ ID NO 34
<211> LENGTH: 500
<212> TYPE: DNA
<213> ORGANISM: Medicago truncatula
<220> FEATURE:
<221> NAME/KEY: misc_feature
<222> LOCATION: (1)..(500)
<223> OTHER INFORMATION: 3' UTR, T-Mt.Sali3-2-1:2:1 derived from the
      Sali3 gene of Medicago truncatula.

<400> SEQUENCE: 34
gagtactctc caacatggac acaccatggg attgtgtaac ataaataatg tgtcgtttgt     60
aatgaatgct cgcaactttt ctagctaatt aagctagagt tgaacttgag ctactttat    120 gtaccctaaa gaggcacaat ctttgctgtt gatgtactat gatcatgtta taatatgatg    180
aaaatggagt gtgcctcatt ttataatttt tattttcctg agtatatgtt tttagggcta    240
aacaccttat aaaaaaggt cacttagaat atgaaacatg aacttttgta aaaaagtaga    300
gattaaaatt gaaatcaaaa attttatag gatcaatatt cgaagaattt ttttagaggg    360
attaaaatta aatatagttt cggactgacc caaggcacaa tccggctccg ctcgggttcg    420
acctgagtcc accatgcatc tgtcacctta ccattgacac gccctaaaat acattagatc    480
gcagtacaaa ttgagagtta                                                500

<210> SEQ ID NO 35
<211> LENGTH: 500
<212> TYPE: DNA
<213> ORGANISM: Medicago truncatula
<220> FEATURE:
<221> NAME/KEY: misc_feature
<222> LOCATION: (1)..(500)
<223> OTHER INFORMATION: 3' UTR, T-Mt.Oxr-1:2:1 derived from a putative
      oxidoreductase (OXR) protein gene from Medicago truncatula.

<400> SEQUENCE: 35
aaatgaatga atcagctttc tcttgttcat aaagaattgt gtggaaatga attgtgtgtt     60
gctatataca tgagtgtgtt ggttgctgcc ttatgtgttc ttctaggt attttttctt    120 ttgctttgta ataatttgtg cgttactatt gtaaacaatg tatttaatga ataatgaaag    180
tctaaagttt gtaatggagg gaagtaaatg taaatccttt cgcaagtgtt ttttagctt    240 gaaagtctttt catgcattgg tttggagtac catcatatca ccccttaattt ttctagttat    300

```
gattttaggg acaagagaag ttcaaattac actccaatta tgtgctcggg gaaatttaat    360
tggtagcaga caatacacga aaaagtaaca catttagtat cttactatca tctgcaaatc    420
gtgcatatgt tcatatcatt tcacattttt ataatccagc atattataaa ttcaaaccta    480
attttggtac ataatagtat                                                500
```

<210> SEQ ID NO 36
<211> LENGTH: 315
<212> TYPE: DNA
<213> ORGANISM: Gossypium barbadense
<220> FEATURE:
<221> NAME/KEY: misc_feature
<222> LOCATION: (1)..(315)
<223> OTHER INFORMATION: 3' UTR, T-Gb.FbL2:1 derived from the Gossypium
      barbadense FbLate-2 gene.

<400> SEQUENCE: 36

```
accatatgac actggtgcat gtgccatcat catgcagtaa tttcatggta tatcttaatt    60
atatggttaa taaaaaaaag atggtgagtg aataatgtgc gtgcattcct ccatgcacca   120
atggtgaatc tctttgcata catagagatt ctgaatgatt atagtttatg ttgtagtgaa   180
attaattttg aatgttgttt ttaaattta atgtcacttg gcttgattta tgttttaacg   240
aagcttatgt tatgtatttt actttaatga tattgcatgt attgttaatt taacattgct   300
tgatcagtat actct                                                    315
```

<210> SEQ ID NO 37
<211> LENGTH: 500
<212> TYPE: DNA
<213> ORGANISM: Medicago truncatula
<220> FEATURE:
<221> NAME/KEY: misc_feature
<222> LOCATION: (1)..(500)
<223> OTHER INFORMATION: 3' UTR, T-Mt.RD22-1:2:1 derived from a
      dehydration-responsive protein RD22 gene from Medicago truncatula.

<400> SEQUENCE: 37

```
aaacaccaat tccatcttct tcaataataa ccactatata tatatagaag caacttcaaa    60
aatacttaat acttgtatta taaattgagt tactttgaat gtcctacgat agagacggag   120
ttcaaatctc ctcaagtatg gttgaaaaat ggtcttcaat gtaactttaa ataaaaactt   180
tgtacgtcct cgctaataaa aataatgttt gtttaattac tttatatatg tattttttaa   240 tgctattttta tatatgttgt accccaaact tgtctgacca atttaatcag aagaacatgt   300
agagtgtagg tttgccggga agatttggat taaagtcttc gtttggttgg gtttggtctt   360
ggtcatgccg gaaaatttat tttccttgta cttcaaatgt tttgcttttt cgatcggaaa   420
gggaatagga gattaaaggg cctcctttta atatggcaaa cagaattata gctttagact   480
gacgctgcgg tttagcttca                                                500
```

<210> SEQ ID NO 38
<211> LENGTH: 1204
<212> TYPE: DNA
<213> ORGANISM: Arabidopsis thaliana
<220> FEATURE:
<221> NAME/KEY: misc_feature
<222> LOCATION: (1)..(1204)
<223> OTHER INFORMATION: EXP-At.Cyco:1:1, derived from a Cytochrome c
      oxidase subunit VIa gene from Arabidopsis.

<400> SEQUENCE: 38

```
tgcgagtggg cgaattccgg agcactctga ttggctgaaa aaatagaaat agtagtgatg    60
```

```
ttgctcctcc tctcctcctc tattattaat ttttcgtcgt tcttcttctg aaagttgtgt    120
ggtttttaga ggtcaccaaa aaaaatctat tttgagatac taaaaatatt tcgttttgca    180
ttttgttgtg cagccatttg ttacacaggt tgaagcttat aactgaaaat tggattcaaa    240
gaatcgtaga tgaagaaatc gaagtgagtt gaatattttc tgaacatatg aaaattggaa    300
caagtttttt ctcatttttgc tagtttcctg tttttatgtt ttcttgactt taggagatga    360
catatggagg tgaactatac aaaggttgtt gcaacgataa cattctcctt aattcagttt    420
ttgcaactcg gttacaagca ctcagtggac ttttggccaa gacaattttt ttttttttt     480 tctctctctc taaaatgtta tagatacgaa tcctttgttg aataaaggaa aaagttgaac    540
atttgattac acataagact ttaacataat ccaactttt tttatatgaa gctacaaaca     600
agatttaaaa catcaaagat tcatctaaa cttcattcat cttcaatctt caacatcctt     660
caatgactag tatgtatgta cataagtaaa attgttgata agaaaacaaa acaatgatgg    720
gctaaaatag cccataaaag gcccattaaa cttgggttta gactttagat tcaacgacgc    780
cagattagtg agtcacataa ccctcttgga aagagtctca acacttgcag agaaaaagaa    840
caaggaagat cccggaaaca ggtaatttct ctcctctcta ttttaccat tttccattga     900 cgacgatcta ggttttctga tttgattttg gagaacgcct cgatgagttt atagattcgt    960
agattggttt tgagattcag tataatttca cccggattcc aattttgaa ccgatacta     1020 attttgaatt gatttggtag atcgattggt caaatttgaa attgattttt ctccataata   1080
tctgaagcgt cttattggat caaatctaca acatttctct gttgaaagga tcgattttt    1140 ttttcttgga acatgataac ttttgattat tcatcaaagt tttgttcttt ttaatatttc   1200
acag                                                                1204
```

<210> SEQ ID NO 39
<211> LENGTH: 786
<212> TYPE: DNA
<213> ORGANISM: Arabidopsis thaliana
<220> FEATURE:
<221> NAME/KEY: misc_feature
<222> LOCATION: (1)..(786)
<223> OTHER INFORMATION: Promoter, P-At.Cyco-1:1:2 derived from a
      Cytochrome c oxidase subunit VIa gene from Arabidopsis.

<400> SEQUENCE: 39

```
tgcgagtggg cgaattccgg agcactctga ttggctgaaa aaatagaaat agtagtgatg     60
ttgctcctcc tctcctcctc tattattaat ttttcgtcgt tcttcttctg aaagttgtgt    120
ggtttttaga ggtcaccaaa aaaaatctat tttgagatac taaaaatatt tcgttttgca    180
ttttgttgtg cagccatttg ttacacaggt tgaagcttat aactgaaaat tggattcaaa    240
gaatcgtaga tgaagaaatc gaagtgagtt gaatattttc tgaacatatg aaaattggaa    300
caagtttttt ctcatttttgc tagtttcctg tttttatgtt ttcttgactt taggagatga    360
catatggagg tgaactatac aaaggttgtt gcaacgataa cattctcctt aattcagttt    420
ttgcaactcg gttacaagca ctcagtggac ttttggccaa gacaattttt ttttttttt     480 tctctctctc taaaatgtta tagatacgaa tcctttgttg aataaaggaa aaagttgaac    540
atttgattac acataagact ttaacataat ccaactttt tttatatgaa gctacaaaca     600
agatttaaaa catcaaagat tcatctaaa cttcattcat cttcaatctt caacatcctt     660
caatgactag tatgtatgta cataagtaaa attgttgata agaaaacaaa acaatgatgg    720
gctaaaatag cccataaaag gcccattaaa cttgggttta gactttagat tcaacgacgc    780
``` cagatt                                                                      786

<210> SEQ ID NO 40
<211> LENGTH: 72
<212> TYPE: DNA
<213> ORGANISM: Arabidopsis thaliana
<220> FEATURE:
<221> NAME/KEY: misc_feature
<222> LOCATION: (1)..(72)
<223> OTHER INFORMATION: Leader, L-At.Cyco-1:1:2 derived from a
      Cytochrome c oxidase subunit VIa gene from Arabidopsis.

<400> SEQUENCE: 40
agtgagtcac ataaccctct tggaaagagt ctcaacactt gcagagaaaa agaacaagga    60
agatcccgga aa                                                        72

<210> SEQ ID NO 41
<211> LENGTH: 346
<212> TYPE: DNA
<213> ORGANISM: Arabidopsis thaliana
<220> FEATURE:
<221> NAME/KEY: misc_feature
<222> LOCATION: (1)..(346)
<223> OTHER INFORMATION: Intron, I-At.Cyco-1:1:1 derived from a
      Cytochrome c oxidase subunit VIa gene from Arabidopsis.

<400> SEQUENCE: 41
caggtaattt ctctcctctc tattttacc attttccatt gacgacgatc taggttttct    60
gatttgattt tggagaacgc ctcgatgagt ttatagattc gtagattggt tttgagattc   120
agtataattt cacccggatt ccaattttg aaccgatacc taattttgaa ttgatttggt    180
agatcgattg gtcaaatttg aaattgattt ttctccataa tatctgaagc gtcttattgg   240
atcaaatcta caacatttct ctgttgaaag gatcgatttt ttttttcttg gaacatgata   300
acttttgatt attcatcaaa gttttgttct tttaatatt tcacag                   346

<210> SEQ ID NO 42
<211> LENGTH: 2001
<212> TYPE: DNA
<213> ORGANISM: Artificial
<220> FEATURE:
<223> OTHER INFORMATION: Coding sequence for beta-glucuronidase (GUS)
      with a processable intron derived from the potato light-inducible
      tissue-specific ST-LS1 gene (Genbank Accession: X04753).

<400> SEQUENCE: 42
atggtccgtc ctgtagaaac cccaacccgt gaaatcaaaa aactcgacgg cctgtgggca    60
ttcagtctgg atcgcgaaaa ctgtggaatt gatcagcgtt ggtgggaaag cgcgttacaa   120
gaaagccggg caattgctgt gccaggcagt tttaacgatc agttcgccga tgcagatatt   180
cgtaattatg cgggcaacgt ctggtatcag cgcgaagtct ttataccgaa aggttgggca   240
ggccagcgta tcgtgctgcg tttcgatgcg gtcactcatt acggcaaagt gtgggtcaat   300
aatcaggaag tgatggagca tcagggcggc tatacgccat tgaagccga tgtcacgccg    360 tatgttattg ccgggaaaag tgtacgtaag tttctgcttc tacctttgat atatatataa   420
taattatcat taattagtag taatataata tttcaaatat ttttttcaaa ataaagaat    480 gtagtatata gcaattgctt ttctgtagtt tataagtgtg tatattttaa tttataactt   540
ttctaatata tgaccaaaat tgttgatgt gcaggtatca ccgttgtgt gaacaacgaa     600 ctgaactggc agactatccc gccgggaatg gtgattaccg acgaaaacgg caagaaaaag   660

```
cagtcttact tccatgattt ctttaactat gccggaatcc atcgcagcgt aatgctctac      720
accacgccga acacctgggt ggacgatatc accgtggtga cgcatgtcgc gcaagactgt      780
aaccacgcgt ctgttgactg gcaggtggtg gccaatggtg atgtcagcgt tgaactgcgt      840
gatgcggatc aacaggtggt tgcaactgga caaggcacta gcgggacttt gcaagtggtg      900
aatccgcacc tctggcaacc gggtgaaggt tatctctatg aactgtgcgt cacagccaaa      960
agccagacag agtgtgatat ctacccgctt cgcgtcggca tccggtcagt ggcagtgaag     1020
ggcgaacagt tcctgattaa ccacaaaccg ttctacttta ctggctttgg tcgtcatgaa     1080
gatgcggact tgcgtggcaa aggattcgat aacgtgctga tggtgcacga ccacgcatta     1140
atggactgga ttggggccaa ctcctaccgt acctcgcatt acccttacgc tgaagagatg     1200
ctcgactggg cagatgaaca tggcatcgtg gtgattgatg aaactgctgc tgtcggcttt     1260
aacctctctt taggcattgg tttcgaagcg ggcaacaagc cgaaagaact gtacagcgaa     1320
gaggcagtca acgggaaaac tcagcaagca cacttacagg cgattaaaga gctgatagcg     1380
cgtgacaaaa accacccaag cgtggtgatg tggagtattg ccaacgaacc ggatacccgt     1440
ccgcaaggtg cacggaaata tttcgcgcca ctggcggaag caacgcgtaa actcgacccg     1500
acgcgtccga tcacctgcgt caatgtaatg ttctgcgacg ctcacaccga taccatcagc     1560
gatctctttg atgtgctgtg cctgaaccgt tattacggat ggtatgtcca agcggcgat      1620 ttggaaacgg cagagaaggt actggaaaaa gaacttctgg cctggcagga gaaactgcat     1680
cagccgatta tcatcaccga atacggcgtg gatacgttag ccgggctgca ctcaatgtac     1740
accgacatgt ggagtgaaga gtatcagtgt gcatggctgg atatgtatca ccgcgtcttt     1800
gatcgcgtca gcgccgtcgt cggtgaacag gtatggaatt cgccgatttt gcgacctcg      1860 caaggcatat tgcgcgttgg cggtaacaag aaagggatct tcactcgcga ccgcaaaccg     1920
aagtcggcgg cttttctgct gcaaaaacgc tggactggca tgaacttcgg tgaaaaaccg     1980
cagcagggag gcaaacaatg a                                               2001
```

<210> SEQ ID NO 43
<211> LENGTH: 928
<212> TYPE: DNA
<213> ORGANISM: Artificial
<220> FEATURE:
<223> OTHER INFORMATION: Synthetic EXP, EXP-At.GSP442+L-I-At.Cyco.

<400> SEQUENCE: 43

```
tgttaatgtt atccgaacta gtcataatta caaccgacaa ataaggttta ttttgtgtgt       60
tatagaattt tttggacagt ttttgttttg gttttcgatt gtagtaaaaa tagatttatg      120
taataagatt tacttttctt gttgaaacaa ataatctta  gaattaactc aacttttatg      180
ttagaacaaa tgataaaaaa atttcccctt ttctatgcga ttattttcaa tcagagagaa      240
atacatataa tatatataat tcaaattaat ctgccaaatt aataaatttg gattaaaatt      300
tataaatgaa acaatggtgt aaggcaatta aaaacacaac actaaaaata tgagaacatt      360
ttatctgggc attaagagtt tgggctttag atctaaaata aaggccggcc caacgagaat      420
attaaaccct aattgaccta gttccctata tataaaacc  ctatatttct ctcgtcactc      480
ctcaactctc agctaaacca cggaccgcag tgagtcacat aaccctcttg gaaagagtct      540
caacacttgc agagaaaaag aacaaggaag atcccggaaa caggtaattt ctctcctctc      600 tattttttacc attttccatt gacgacgatc taggttttct gatttgattt tggagaacgc      660
ctcgatgagt ttatagattc gtagattggt tttgagattc agtataattt cacccggatt      720
```

```
ccaattttt g aaccgatacc taattttgaa ttgatttggt agatcgattg gtcaaatttg    780
aaattgattt ttctccataa tatctgaagc gtcttattgg atcaaatcta caacatttct    840
ctgttgaaag gatcgatttt tttttcttg gaacatgata acttttgatt attcatcaaa     900
gttttgttct ttttaatatt tcacaggt                                        928
```

```
<210> SEQ ID NO 44
<211> LENGTH: 300
<212> TYPE: DNA
<213> ORGANISM: Artificial
<220> FEATURE:
<223> OTHER INFORMATION: Synthetic 3' UTR, T-Zm.GST7.nno:2.

<400> SEQUENCE: 44
atgtctgctg cggcggcctt cacagtttgt ttatttccta ctgtttgctg cggcgattgt     60
tgttgttttc tgttttataa ataataaagg aggaggagat ttgttttggt ttgtgtttgt    120
ttccatcctt gctgctccat cacactatct gtaatttgta aacagcgaca ataaataaat    180
taataaattt ggtttctcat acctatatgt gtctgtttgg aggcttgttt gtttgagaca    240
tctgtctggt tgttttttg ctgccagccg gtagtataaa ttttgttttt ggacgacgaa    300
```

```
<210> SEQ ID NO 45
<211> LENGTH: 855
<212> TYPE: DNA
<213> ORGANISM: Artificial
<220> FEATURE:
<223> OTHER INFORMATION: Synthetic EXP, EXP-At.GSP576.nno+At.Cyco:1.

<400> SEQUENCE: 45
aattaaattc aacacgtttg ttatatattt tttattgaaa ttattcttca ttcgtctttt     60
aatggataaa aaggtataat caagtatatt ttatacacat ctttctattt gtgtgtacca    120
aatgttaaaa tggccaattt tgaccaaaaa accgcataat tttcttaatt tcttaaatat    180
gattaattca tcaataactt ggaatttcac aatacacaaa agtgggtgta gttaccgtta    240
ttatatttat acacaacaac tcatctcctc atagaaagaa aagaaaaata aaataagaaa    300
tcaaaaaacg acaagataac caatctccac atcatccacg tggcgtaagg ataaggtcac    360
aaccaccact cagccacgtg gcagaatctt atccaatcac tctcaccaca caaaccttat    420
ccacttctat atataatctc ttcttctcat tatcactcac cacacatcct tgcaaaagta    480
aagagaaaaa acaaacaaga cggaccgcag gtaatttctc tcctctctat ttttaccatt    540
ttccattgac gacgatctag gttttctgat ttgattttgg agaacgcctc gatgagttta    600
tagattcgta gattggtttt gagattcagt ataatttcac ccggattcca atttttgaac    660
cgatacctaa ttttgaattg atttggtaga tcgattggtc aaatttgaaa ttgatttttc    720
tccataatat ctgaagcgtc ttattggatc aaatctacaa catttctctg ttgaaaggat    780
cgattttttt tttcttggaa catgataact tttgattatt catcaaagtt ttgttctttt    840
taatatttca caggt                                                      855
```

```
<210> SEQ ID NO 46
<211> LENGTH: 835
<212> TYPE: DNA
<213> ORGANISM: Cauliflower mosaic virus
<220> FEATURE:
<221> NAME/KEY: misc_feature
<222> LOCATION: (1)..(835)
<223> OTHER INFORMATION: DNA sequence of the EXP, EXP-CaMV.35S
      comprising the 35S promoter and leader derived from the
```

Cauliflower mosaic virus.

<400> SEQUENCE: 46

```
agattagcct tttcaatttc agaaagaatg ctaacccaca gatggttaga gaggcttacg      60
cagcaggtct catcaagacg atctacccga gcaataatct ccaggaaatc aaataccttc     120
ccaagaaggt taaagatgca gtcaaaagat tcaggactaa ctgcatcaag aacacagaga     180
aagatatatt tctcaagatc agaagtacta ttccagtatg gacgattcaa ggcttgcttc     240
acaaaccaag gcaagtaata gagattggag tctctaaaaa ggtagttccc actgaatcaa     300
aggccatgga gtcaaagatt caaatagagg acctaacaga actcgccgta agactggcg      360
aacagttcat acagagtctc ttacgactca atgacaagaa gaaaatcttc gtcaacatgg     420
tggagcacga cacacttgtc tactccaaaa atatcaaaga tacagtctca gaagaccaaa     480
gggcaattga gacttttcaa caaagggtaa tatccggaaa cctcctcgga ttccattgcc     540
cagctatctg tcactttatt gtgaagatag tggaaaagga aggtggctcc tacaaatgcc     600
atcattgcga taaggaaag gccatcgttg aagatgcctc tgccgacagt ggtcccaaag      660
atggaccccc acccacgagg agcatcgtgg aaaaagaaga cgttccaacc acgtcttcaa     720
agcaagtgga ttgatgtgat atctccactg acgtaaggga tgacgcacaa tcccactatc     780
cttcgcaaga cccttcctct atataaggaa gttcatttca tttggagagg acacg          835
```

<210> SEQ ID NO 47
<211> LENGTH: 804
<212> TYPE: DNA
<213> ORGANISM: Zea mays
<220> FEATURE:
<221> NAME/KEY: misc_feature
<222> LOCATION: (1)..(804)
<223> OTHER INFORMATION: DNA sequence of the intron, I-Zm.DnaK:1, derived from the heat shock protein 70 (Hsp70) gene (DnaK) from corn.

<400> SEQUENCE: 47

```
accgtcttcg gtacgcgctc actccgccct ctgcctttgt tactgccacg tttctctgaa      60
tgctctcttg tgtggtgatt gctgagagtg gtttagctgg atctagaatt acactctgaa     120
atcgtgttct gcctgtgctg attacttgcc gtcctttgta gcagcaaaat atagggacat     180
ggtagtacga aacgaagata gaacctacac agcaatacga gaaatgtgta atttggtgct     240
tagcggtatt tatttaagca catgttggtg ttatagggca cttggattca gaagtttgct     300
gttaatttag gcacaggctt catactacat gggtcaatag tatagggatt catattatag     360
gcgatactat aataatttgt tcgtctgcag agcttattat ttgccaaaat tagatattcc     420
tattctgttt ttgtttgtgt gctgttaaat tgttaacgcc tgaaggaata aatataaatg     480
acgaaatttt gatgtttatc tctgctcctt tattgtgacc ataagtcaag atcagatgca     540
cttgttttaa atattgttgt ctgaagaaat aagtactgac agtatttga tgcattgatc       600
tgcttgtttg ttgtaacaaa atttaaaaat aaagagtttc cttttgttg ctctccttac       660
ctcctgatgg tatctagtat ctaccaactg acactatatt gcttctcttt acatacgtat     720
cttgctcgat gccttctccc tagtgttgac cagtgttact cacatagtct ttgctcattt     780
cattgtaatg cagataccaa gcgg                                            804
```

<210> SEQ ID NO 48
<211> LENGTH: 300
<212> TYPE: DNA
<213> ORGANISM: Orzya sativa

```
<220> FEATURE:
<221> NAME/KEY: misc_feature
<222> LOCATION: (1)..(300)
<223> OTHER INFORMATION: DNA sequence of the 3' UTR, T-Os.LTP:1, derived
      from the Lipid Transfer Protein-like gene (LTP) from rice .

<400> SEQUENCE: 48
attaatcgat cctccgatcc cttaattacc ataccattac accatgcatc aatatccata      60
tatatataaa ccctttcgca cgtacttata ctatgttttg tcatacatat atatgtgtcg     120
aacgatcgat ctatcactga tatgatatga ttgatccatc agcctgatct ctgtatcttg     180
ttatttgtat accgtcaaat aaaagtttct tccacttgtg ttaataatta gctactctca     240
tctcatgaac cctatatata actagtttaa tttgctgtca attgaacatg atgatcgatg     300

<210> SEQ ID NO 49
<211> LENGTH: 516
<212> TYPE: DNA
<213> ORGANISM: Artificial
<220> FEATURE:
<223> OTHER INFORMATION: Coding sequence for an engineered luciferase
      flourescent protein.

<400> SEQUENCE: 49
atggtcttca cactcgaaga tttcgttggg gactggcgac agacagccgg ctacaacctg      60
gaccaagtcc ttgaacaggg aggtgtgtcc agtttgtttc agaatctcgg ggtgtccgta     120
actccgatcc aaaggattgt cctgagcggt gaaaatgggc tgaagatcga catccatgtc     180
atcatcccgt atgaaggtct gagcggcgac caaatgggcc agatcgaaaa aattttttaag    240 gtggtgtacc ctgtggatga tcatcacttt aaggtgatcc tgcactatgg cacactggta     300
atcgacgggg ttacgccgaa catgatcgac tatttcggac ggccgtatga aggcatcgcc     360
gtgttcgacg gcaaaaagat cactgtaaca gggaccctgt ggaacggcaa caaaattatc     420
gacgagcgcc tgatcaaccc cgacggctcc ctgctgttcc gagtaaccat caacggagtg     480
accggctggc ggctgtgcga acgcattctg gcgtaa                                516

<210> SEQ ID NO 50
<211> LENGTH: 1848
<212> TYPE: DNA
<213> ORGANISM: Artificial
<220> FEATURE:
<223> OTHER INFORMATION: DNA sequence of the EXP, EXP-At.Bglu21+At.Cyco:
      2 comprising the promoter and leader of a beta-glucuronidase 21
      gene from Arabidopsis thaliana, operably linked 5' to the intron,
      I-At.Cyco-1:1:1.

<400> SEQUENCE: 50
aaataaattt cttaaagtgt gtgttttaat ctaaaacatc atataatttg aaatagagga      60
aatatcatct aataaagtaa tggtatattt gtatagttaa tgatttgtct ttttattcgc     120
gcaaaatgtg tcaattataa aatataaaga ggatataatt tagtttagag ttttagacac     180
gaggactata tattggaaaa caaaaaagta atgtaaacca tatagatcat ggaatgagtc     240
atcctattaa acagttgtat tatatattta tatttagtc actaacacat taataactta      300
acgtccataa caaaataaga tccaaaactc gatctagatc tatacgaggc actaaatgat     360
ccattgactt agggccggcc gattggttcg aggactcctc atgctgtaaa cttttttttt     420
ggacatacat gatataattt taagtcacgt ttttatatta tatgttccac gcccaatata     480
atatgttcca aactaggaaa aataagtaag aattagtcaa tgatcgagat aatgcaatga     540
atcatcctat ttattaaata gatttactaa actatatata atacaatgat cgagatcgtg     600
```

```
ccatgaagca tcctatatac tataaaaata gtcttactaa atacatactc atatagttta      660
gtcattcatt agtccaaaca ttaaatgaga gatcctttac ttgctacctg aattttttca      720
gaataaggta taacttttt  tcgaattaga aactgattta tgaaagatta agagtaatgt      780
tcgttaaaca agttaaaaaa tatgttttta caattaagtt ttgaaaaata ataaagtctc      840
caattatttg agtatcaaaa ataggcttgt tattatttag ggttttcgtt ggtttaaatg      900
caacggggtg tggttgtcat tgtggaagtt aatggaagta attggttgag gttttaaacg      960
ttatcggaca ttttaaatga ctggtttaca gttaaaaata tgtgtattta cggcaatttt     1020
atgattggct tagcagtaga tgcgacagtg gtttaaacca aaaattacca aataaataat     1080
atacaattat taaattatat aaaacaccaa tattatatat ttatatatat atgaacatag     1140
ttaattatcg aaaccataga caaagtacat aagagttatt ccgaaaaagg tttattatga     1200
aacacaaata atcatattgg gagattatga tatccaaaat ggactaatca aataattaaa     1260
tccaaaatgg atgaagaact tatattagtt ccacgcacaa tataatatgt tccaaactaa     1320
gtaagaacac aacggtcgag gtcatgcaat gaatcatcct atatataaaa tagttttact     1380
aaacaattat attttagtca ctcgttaaca aacaatcaaa atcgctatat aaagaactcc     1440
gattggatgt aaacaaatca tcataaactt gttctcttcc agaagaaact aaaaacaaaa     1500
caggtaattt ctctcctctc tattttttacc attttccatt gacgacgatc taggttttct     1560
gatttgattt tggagaacgc ctcgatgagt ttatagattc gtagattggt tttgagattc     1620
agtataattt cacccggatt ccaattttg  aaccgatacc taattttgaa ttgatttggt     1680
agatcgattg gtcaaatttg aaattgattt ttctccataa tatctgaagc gtcttattgg     1740
atcaaatcta caacatttct ctgttgaaag gatcgatttt tttttcttg  gaacatgata     1800 actttgatt  attcatcaaa gttttgttct tttaatatt  tcacaggt              1848
```

<210> SEQ ID NO 51
<211> LENGTH: 712
<212> TYPE: DNA
<213> ORGANISM: Artificial
<220> FEATURE:
<223> OTHER INFORMATION: DNA sequence of the EXP, EXP-CaMV.35S-enh+Ph.
      DnaK:1:3 comprising an enhanced Cauliflower mosaic virus 35S
      promoter, operably linked 5' to the leader of the heat shock
      protein 70 (HSP70) gene from Petunia.

<400> SEQUENCE: 51

```
ggtccgatgt gagactttc  aacaaagggt aatatccgga aacctcctcg gattccattg       60
cccagctatc tgtcactta  ttgtgaagat agtggaaaag gaaggtggct cctacaaatg      120
ccatcattgc gataaaggaa aggccatcgt gaagatgcc  tctgccgaca gtggtcccaa      180
agatggaccc ccacccacga ggagcatcgt ggaaaaagaa gacgttccaa ccacgtcttc      240
aaagcaagtg gattgatgtg atggtccgat tgagactttt caacaaaggg taatatccgg      300
aaacctcctc ggattccatt gcccagctat ctgtcacttt attgtgaaga tagtggaaaa      360
ggaaggtggc tcctacaaat gccatcattg cgataaagga aaggccatcg ttgaagatgc      420
ctctgccgac agtggtccca agatggaccc ccacccacg  aggagcatcg tggaaaaaga      480
agacgttcca accacgtctt caaagcaagt ggattgatgt gatatctcca ctgacgtaag      540
ggatgacgca aatcccact  atccttcgca agacccttcc tctatataag gaagttcatt      600
tcatttggag aggacactct agacagaaaa atttgctaca ttgttcaca  aacttcaaat      660 attattcatt tatttgtcag ctttcaaact ctttgtttct tgtttgttga tt              712
```

<210> SEQ ID NO 52
<211> LENGTH: 841
<212> TYPE: DNA
<213> ORGANISM: Glycine max
<220> FEATURE:
<221> NAME/KEY: misc_feature
<222> LOCATION: (1)..(841)
<223> OTHER INFORMATION: DNA sequence of the EXP, EXP-Gm.Sphas1:1:1 comprising the promoter and leader of the 7S alpha prime gene of soybean.

<400> SEQUENCE: 52

```
ggcaaaaaca tttaatacgt attatttaag aaaaaaatat gtaataatat atttatattt      60
taatatctat tcttatgtat tttttaaaaa tctattatat attgatcaac taaaatattt     120
ttatatctac acttattttg cattttatc aatttcttg cgttttttgg catatttaat      180
aatgactatt ctttaataat caatcattat tcttacatgg tacatattgt tggaaccata    240
tgaagtgtcc attgcatttg actatgtgga tagtgttttg atccaggcct ccatttgccg    300
cttattaatt aatttggtaa cagtccgtac taatcagtta cttatccttc ctccatcata    360
attaatcttg gtagtctcga atgccacaac actgactagt ctcttggatc ataagaaaaa    420
gccaaggaac aaaagaagac aaaacacaat gagagtatcc tttgcatagc aatgtctaag    480
ttcataaaat tcaaacaaaa acgcaatcac acacagtgga catcacttat ccactagctg    540
atcaggatcg ccgcgtcaag aaaaaaaaac tggaccccaa aagccatgca caacaacacg    600
tactcacaaa ggtgtcaatc gagcagccca aacattcac caactcaacc catcatgagc     660
ccacacattt gttgtttcta acccaacctc aaactcgtat tctcttccgc cacctcattt    720
ttgtttattt caacacccgt caaactgcat gccaccccgt ggccaaatgt ccatgcatgt    780
taacaagacc tatgactata aatatctgca atctcggccc aggttttcat catcaagaac    840
c                                                                    841
```

<210> SEQ ID NO 53
<211> LENGTH: 1446
<212> TYPE: DNA
<213> ORGANISM: Artificial
<220> FEATURE:
<223> OTHER INFORMATION: DNA sequence of the EXP, EXP-CaMV.35S-enh+Zm.DnaK:1:1 comprising an enhanced Cauliflower mosaic virus 35S promoter, operably linked 5' to the intron, I-Zm.DnaK:1.

<400> SEQUENCE: 53

```
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa    180
gatggacccc cacccacgag gagcatcgtg aaaaagaag acgttccaac cacgtcttca     240
aagcaagtgg attgatgtga tgtccgatt gagacttttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacgctg acaagctgac tctagcagat ctaccgtctt cggtacgcgc    660
```

| | |
|---|---|
| tcactccgcc ctctgccttt gttactgcca cgtttctctg aatgctctct tgtgtggtga | 720 |
| ttgctgagag tggtttagct ggatctagaa ttacactctg aaatcgtgtt ctgcctgtgc | 780 |
| tgattacttg ccgtcctttg tagcagcaaa atatagggac atggtagtac gaaacgaaga | 840 |
| tagaacctac acagcaatac gagaaatgtg taatttggtg cttagcggta tttatttaag | 900 |
| cacatgttgg tgttataggg cacttggatt cagaagtttg ctgttaattt aggcacaggc | 960 |
| ttcatactac atgggtcaat agtataggga ttcatattat aggcgatact ataataattt | 1020 |
| gttcgtctgc agagcttatt atttgccaaa attagatatt cctattctgt ttttgtttgt | 1080 |
| gtgctgttaa attgttaacg cctgaaggaa taaatataaa tgacgaaatt ttgatgttta | 1140 |
| tctctgctcc tttattgtga ccataagtca agatcagatg cacttgtttt aaatattgtt | 1200 |
| gtctgaagaa ataagtactg acagtatttt gatgcattga tctgcttgtt tgttgtaaca | 1260 |
| aaatttaaaa ataaagagtt tccttttgt tgctctcctt acctcctgat ggtatctagt | 1320 |
| atctaccaac tgacactata ttgcttctct ttacatacgt atcttgctcg atgccttctc | 1380 |
| cctagtgttg accagtgtta ctcacatagt ctttgctcat tcattgtaa tgcagatacc | 1440 |
| aagcgg | 1446 |

<210> SEQ ID NO 54
<211> LENGTH: 1653
<212> TYPE: DNA
<213> ORGANISM: Photinus pyralis
<220> FEATURE:
<221> NAME/KEY: misc_feature
<222> LOCATION: (1)..(1653)
<223> OTHER INFORMATION: DNA sequence encoding a luciferase protein derived from Firefly.

<400> SEQUENCE: 54

| | |
|---|---|
| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aaggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg atatttgat atgtggattt | 780 |
| cgagtcgtct taatgtatag atttgaagaa gagctgtttt tacgatccct tcaggattac | 840 |
| aaaattcaaa gtgcgttgct agtaccaacc ctattttcat tcttcgccaa aagcactctg | 900 |
| attgacaaat acgatttatc taatttacac gaaattgctt ctggggggcgc acctctttcg | 960 |
| aaagaagtcg ggaagcggt tgcaaaacgc ttccatcttc cagggatacg acaaggatat | 1020 |
| gggctcactg agactacatc agctattctg attacacccg agggggatga taaaccgggc | 1080 |
| gcggtcggta agttgttcc attttttgaa gcgaaggttg tggatctgga taccgggaaa | 1140 |

```
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                 1653

<210> SEQ ID NO 55
<211> LENGTH: 253
<212> TYPE: DNA
<213> ORGANISM: Agrobacterium tumefaciens
<220> FEATURE:
<221> NAME/KEY: misc_feature
<222> LOCATION: (1)..(253)
<223> OTHER INFORMATION: DNA sequence of the 3' UTR, T-AGRtu.nos-1:1:13
      derived from the Agrobacterium tumefaciens nopaline synthase gene.

<400> SEQUENCE: 55
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg gtttttatg attagagtcc cgcaattata catttaatac    180
gcgatagaaa acaaaatata gcgcgcaaac taggataaat tatcgcgcgc ggtgtcatct    240
atgttactag atc                                                       253

<210> SEQ ID NO 56
<211> LENGTH: 675
<212> TYPE: DNA
<213> ORGANISM: Artificial
<220> FEATURE:
<223> OTHER INFORMATION: DNA sequence of the EXP,  EXP-CaMV.35S-enh-
      Lhcb1 comprising an enhanced Cauliflower mosaic virus 35S
      promoter, operably linked 5' to the leader of a chlorophyll
      a/b-binding gene of the light-harvesting complex of wheat.

<400> SEQUENCE: 56
ggtccgatgt gagactttc aacaaagggt aatatccgga aacctcctcg gattccattg     60
cccagctatc tgtcactta ttgtgaagat agtggaaag gaaggtggct cctacaaatg    120
ccatcattgc gataaaggaa aggccatcgt tgaagatgcc tctgccgaca gtggtcccaa    180
agatggaccc ccacccacga ggagcatcgt ggaaaaagaa gacgttccaa ccacgtcttc    240
aaagcaagtg gattgatgtg atggtccgat gtgagacttt tcaacaaagg gtaatatccg    300
gaaacctcct cggattccat tgcccagcta tctgtcactt tattgtgaag atagtggaaa    360
aggaaggtgg ctcctacaaa tgccatcatt gcgataaagg aaaggccatc gttgaagatg    420
cctctgccga cagtggtccc aaagatggac ccccacccac gaggagcatc gtggaaaaag    480
aagacgttcc aaccacgtct tcaaagcaag tggattgatg tgatatctcc actgacgtaa    540
gggatgacgc acaatcccac tatccttcgc aagacccttc ctctatataa ggaagttcat    600
ttcatttgga gaggaaccat cttccacaca ctcaagccac actattggag aacacacagg    660
gacaacacac cataa                                                     675
```

-continued

```
<210> SEQ ID NO 57
<211> LENGTH: 936
<212> TYPE: DNA
<213> ORGANISM: Renilla reniformis
<220> FEATURE:
<221> NAME/KEY: misc_feature
<222> LOCATION: (1)..(936)
<223> OTHER INFORMATION: DNA sequence encoding a luciferase protein
      derived from Sea Pansey.

<400> SEQUENCE: 57
atggcttcca aggtgtacga ccccgagcaa cgcaaacgca tgatcactgg gcctcagtgg        60
tgggctcgct gcaagcaaat gaacgtgctg gactccttca tcaactacta tgattccgag       120
aagcacgccg agaacgccgt gatttttctg catggtaacg ctgcctccag ctacctgtgg       180
aggcacgtcg tgcctcacat cgagcccgtg gctagatgca tcatccctga tctgatcgga       240
atgggtaagt ccggcaagag cgggaatggc tcatatcgcc tcctggatca ctacaagtac       300
ctcaccgctt ggttcgagct gctgaacctt ccaaagaaaa tcatctttgt gggccacgac       360 tgggggggctt gtctggcctt tcactactcc tacgagcacc aagacaagat caaggccatc       420
gtccatgctg agagtgtcgt ggacgtgatc gagtcctggg acgagtggcc tgacatcgag       480
gaggatatcg ccctgatcaa gagcgaagag ggcgagaaaa tggtgcttga gaataacttc       540
ttcgtcgaga ccatgctccc aagcaagatc atgcggaaac tggagcctga ggagttcgct       600
gcctacctgg agccattcaa ggagaagggc gaggttagac ggcctaccct ctcctggcct       660
cgcgagatcc ctctcgttaa gggaggcaag cccgacgtcg tccagattgt ccgcaactac       720
aacgcctacc ttcgggccag cgacgatctg cctaagatgt tcatcgagtc cgaccctggg       780
ttcttttcca acgctattgt cgagggagct aagaagttcc ctaacaccga gttcgtgaag       840
gtgaagggcc tccacttcag ccaggaggac gctccagatg aaatgggtaa gtacatcaag       900
agcttcgtgg agcgcgtgct gaagaacgag cagtaa                                 936
```